US006469155B1

(12) United States Patent
Fiume et al.

(10) Patent No.: US 6,469,155 B1
(45) Date of Patent: Oct. 22, 2002

(54) HIGR AND RELATED DOMAIN WHICH BINDS GLYCOPROTEIN D OF HERPES SIMPLEX VIRUS

(75) Inventors: Gabriella Campadelli Fiume, Bologna (IT); Francesca Cocchi, Sasso Marconi (IT); Laura Menotti, Bologna (IT); Marc Lopez, Marseilles (FR)

(73) Assignees: Universita' Degli Studi di Bologna, Bologna (IT); Inserm Institut National de la Sante et de la Recherche Medicale, Paris (FR)

( * ) Notice: Subject to any disclaimer, the term of this patent is extended or adjusted under 35 U.S.C. 154(b) by 0 days.

(21) Appl. No.: 09/435,956

(22) Filed: Nov. 9, 1999

(30) Foreign Application Priority Data

Nov. 10, 1998 (EP) .............................................. 98830677

(51) Int. Cl.[7] .......................... C07H 21/04; C07H 21/02
(52) U.S. Cl. ...................................... 536/23.5; 536/23.1
(58) Field of Search .............................. 536/23.1, 23.4, 536/23.5, 24.1

(56) References Cited

PUBLICATIONS

G Bernhardt et al., Virology, "The Poliovirus Receptor: Identification of Domains and Amino Acid Residues Critical for Virus Binding," (1994), 203, pp. 344–356.*

C. Krummenacher et al.: "Herpes simplex virus glycoprotein D can bind to poliovirus receptor–related protein 1 or herpesvirus entry mediator, 2 structurally unrelated mediators of virus entry." Journal of Virology, vol. 72, No. 9, Sep. 98, pp. 7064–7074, XP002114162 Abstract Fig. 1 p. 7064, right–hand column, line 10–p. 7065, left–hand column, line 28 p. 7065, left–hand column, line 67–line 73.

R. Geraghty et al.: "Entry of alphaherpesviruses mediated by poliovirus receptor–related protein 1 and poliovirus receptor". Science vol. 280 No. 5369, Jun. 5, 1998 pp. 1618–1620, XP002114163 Washington, DC, USA the whole document..

M. Lopez et al.: "Complementary DNA characterization and chromosomal localization of a human gene related to the poliovirus receptor–encoding gene". Gene, vol. 155 No. 2, Apr. 3, 1995, pp. 261–265, XP002114164 Amsterdam NL abstract Figures 1,2.

T. Huang et al.: "Anti–idiotypic antibodies mimicking glycoprotein D of herpes simplex virus identify a cellular protein required for virus spread from cell to cell and virus–induced polykaryocytosis"; Proceedings of the National Academy of Sciences of the U.S.A., vol. 93, No. 5, Mar. 5, 1996, pp. 1836–1840, XP002114165 Washington DC U.S.A. abstract.

M. Lopez et al.: "Description of a new antigen family expressed on CD34+hematopoietic progenitors", Tissue Antigens, vol. 48, No. 4 part 2, 1996, p. 428 XP002114166 Copenhagen, DK abstract MC–4–03.

F.Cocchi et al.: "The V domain of herpesvirus Ig–like receptor(HIgR) contains a major functional region in herpes simplex virus–1 entry into cells and interacts physically with the viral glycoprotein D". Proceedings of the national academy of sciences of the U.S.A., vol. 95 No. 26, Dec. 22, 1998 pp. 15700–15705, XP002114167 Washington DC USA the whole document.

F. Cocchi et al.: "The ectodomain of a novel member of the immunoglobulin subfamily related to the poliovirus receptor has the attributes of a bona fide receptor for herpes simplex virus types 1 and 2 in human cells". Journal of virology, vol. 72, No. 12, Dec. 1998 pp. 9992–10002, XP002114168 the whole document.

* cited by examiner

*Primary Examiner*—Deborah Crouch
*Assistant Examiner*—Joseph T. Woitach
(74) *Attorney, Agent, or Firm*—Rockey, Milnamow & Katz, Ltd.

(57) ABSTRACT

The present invention relates to an immunoglobulin-like protein useful in preventing or treating pathologies concerned with herpes simplex virus 1, herpes simplex virus 2 infections in humans.

1 Claim, 10 Drawing Sheets

β-ACTIN

FIG. 7

FIG. 8

INHIBITION OF CELL-TO-CELL SPREAD BY MAb R1.302

INHIBITION OF CELL-TO-CELL SPREAD BY MAb VCC1 - Fc e V1 - Fc

SEQUENCE LISTING

<160> NUMBER OF SEQ ID NOS: 2

<210> SEQ ID NO 1
<211> LENGTH: 458
<212> TYPE: PRT
<213> ORGANISM: Homo sapiens
<220> FEATURE:
<223> OTHER INFORMATION: Original Source:  Hela Cell Line
<223> OTHER INFORMATION: General Functional Class of Gene:
      Immunoglobulin Superfamily
<223> OTHER INFORMATION: Binding Macromolecules:  HSV-gD
<223> OTHER INFORMATION: Subcellular localisation:  Plasma Membrane
<223> OTHER INFORMATION: Other Information:  Viral Receptor

<400> SEQUENCE: 1

Met Ala Arg Met Gly Leu Ala Gly Ala Ala Gly Arg Trp Trp Gly Leu
 1               5                  10                  15

Ala Leu Gly Leu Thr Ala Phe Phe Leu Pro Gly Val His Ser Gln Val
             20                  25                  30

Val Gln Val Asn Asp Ser Met Tyr Gly Phe Ile Gly Thr Asp Val Val
         35                  40                  45

Leu His Cys Ser Phe Ala Asn Pro Leu Pro Ser Val Lys Ile Thr Gln
     50                  55                  60

Val Thr Trp Gln Lys Ser Thr Asn Gly Ser Lys Gln Asn Val Ala Ile
 65                  70                  75                  80

Tyr Asn Pro Ser Met Gly Val Ser Val Leu Ala Pro Tyr Arg Glu Arg
                 85                  90                  95

Val Glu Phe Leu Arg Pro Ser Phe Thr Asp Gly Thr Ile Arg Leu Ser
            100                 105                 110

Arg Leu Glu Leu Glu Asp Glu Gly Val Tyr Ile Cys Gly Phe Ala Thr
        115                 120                 125

Phe Pro Thr Gly Asn Arg Glu Ser Gln Leu Asn Leu Thr Val Met Ala
    130                 135                 140

Lys Pro Thr Asn Trp Ile Glu Gly Thr Gln Ala Val Leu Arg Ala Lys
145                 150                 155                 160

Lys Gly Gln Asp Asp Lys Val Leu Val Ala Thr Cys Thr Ser Ala Asn
                165                 170                 175

Gly Lys Pro Pro Ser Val Val Ser Trp Glu Thr Arg Leu Lys Gly Glu
            180                 185                 190

```
Ala Glu Tyr Gln Glu Ile Arg Asn Pro Asn Gly Thr Val Thr Val Ile
            195                 200                 205
Ser Arg Tyr Arg Leu Val Pro Ser Arg Glu Ala His Gln Gln Ser Leu
    210                 215                 220
Ala Cys Ile Val Asn Tyr His Met Asp Arg Phe Lys Glu Ser Leu Thr
225                 230                 235                 240
Leu Asn Val Gln Tyr Glu Pro Glu Val Thr Ile Glu Gly Phe Asp Gly
                245                 250                 255
Asn Trp Tyr Leu Gln Arg Met Asp Val Lys Leu Thr Cys Lys Ala Asp
            260                 265                 270
Ala Asn Pro Pro Ala Thr Glu Tyr His Trp Thr Thr Leu Asn Gly Ser
        275                 280                 285
Leu Pro Lys Gly Val Glu Ala Gln Asn Arg Thr Leu Phe Phe Lys Gly
    290                 295                 300
Pro Ile Asn Tyr Ser Leu Ala Gly Thr Tyr Ile Cys Glu Ala Thr Asn
305                 310                 315                 320
Pro Ile Gly Thr Arg Ser Gly Gln Val Glu Val Asn Ile Thr Glu Lys
                325                 330                 335
Pro Arg Pro Gln Arg Gly Leu Gly Ser Ala Ala Arg Leu Leu Ala Gly
            340                 345                 350
Thr Val Ala Val Phe Leu Ile Leu Val Ala Val Leu Thr Val Phe Phe
        355                 360                 365
Leu Tyr Asn Arg Gln Gln Lys Ser Pro Pro Glu Thr Asp Gly Ala Gly
    370                 375                 380
Thr Asp Gln Pro Leu Ser Gln Lys Pro Glu Pro Ser Pro Ser Arg Gln
385                 390                 395                 400
Ser Ser Leu Val Pro Glu Asp Ile Gln Val Val His Leu Asp Pro Gly
                405                 410                 415
Arg Gln Gln Gln Glu Glu Glu Asp Leu Gln Lys Leu Ser Leu Gln
            420                 425                 430
Pro Pro Tyr Tyr Asp Leu Gly Val Ser Pro Ser Tyr His Pro Ser Val
        435                 440                 445
Arg Thr Thr Glu Pro Arg Gly Glu Cys Pro
    450                 455

<210> SEQ ID NO 2
<211> LENGTH: 1377
<212> TYPE: DNA
<213> ORGANISM: Homo sapiens
<220> FEATURE:
<223> OTHER INFORMATION: Original Source:  Hela Cell Line
<223> OTHER INFORMATION: General Functional Class of the Gene:
      Immunoglobulin
<223> OTHER INFORMATION: Binding Macromolecules:  HSV-gD
<223> OTHER INFORMATION: Subcellular localisation:  Plasma membrane
<223> OTHER INFORMATION: Other Information:  Viral Receptor
<223> OTHER INFORMATION: Library:  Invitrogen pcDNA 9.1 library
<223> OTHER INFORMATION: Chromsome/segment:  Human Chromosome 11

<400> SEQUENCE: 2
atggctcgga tgggcttgc gggcgccgct ggacgctggt ggggactcgc tctcggcttg      60
accgcattct tcctcccagg cgtccactcc caggtggtcc aggtgaacga ctccatgtat    120
ggcttcatcg gcacagacgt ggttctgcac tgcagctttg ccaacccgct tcccagcgtg    180
aagatcaccc aggtcacatg gcagaagtcc accaatggct ccaagcagaa cgtggccatc    240
tacaacccat ccatgggcgt gtccgtgctg gctccctacc gcgagcgtgt ggaattcctg    300
```

```
cggccctcct tcaccgatgg cactatccgc ctctcccgcc tggagctgga ggatgagggt    360
gtctacatct gcgagtttgc taccttccct acgggcaatc gagaaagcca gctcaatctc    420
acggtgatgg ccaaacccac caattggata gagggtaccc aggcagtgct tcgagccaag    480
aaggggcagg atgacaaggt cctggtggcc acctgcacct cagccaatgg gaagcctccc    540
agtgtggtat cctgggaaac tcggttaaaa ggtgaggcag agtaccagga gatccggaac    600
cccaatggca cagtgacggt catcagccgc taccgcctgg tgcccagcag ggaagcccac    660
cagcagtcct tggcctgcat cgtcaactac cacatggacc gcttcaagga aagcctcact    720
ctcaacgtgc agtatgagcc tgaggtaacc attgaggggt ttgatggcaa ctggtacctg    780
cagcggatgg acgtgaagct cacctgcaaa gctgatgcta accccccagc cactgagtac    840
cactggacca cgctaaatgg ctctctcccc aagggtgtgg aggcccagaa cagaaccctc    900
ttcttcaagg gacccatcaa ctacagcctg gcagggacct acatctgtga ggccaccaac    960
cccatcggta cacgctcagg ccaggtggag gtcaatatca cagaaaagcc ccgcccccag   1020
aggggtctgg gaagtgcagc caggctcctg gcgggcaccg tggccgtgtt cctcatccta   1080
gttgctgtgc tcactgtctt cttcctgtac aaccggcagc agaagagccc accggagacg   1140
gatggggccg ggaccgacca gcccctctcc cagaagccgg agccttctcc cagcaggcaa   1200
agctcccttg tgcctgagga tatccaggtt gtccacctgg acccagggag gcagcagcag   1260
caagaagagg aggacttgca gaagctgtcc ctgcagcccc cctactatga tctgggggtc   1320
tccccctcct accacccctc ggtaaggaca accgaacctc gaggagagtg cccctag      1377
```

HIGR AND RELATED DOMAIN WHICH BINDS GLYCOPROTEIN D OF HERPES SIMPLEX VIRUS

BACKGROUND OF THE INVENTION

Figure 1:
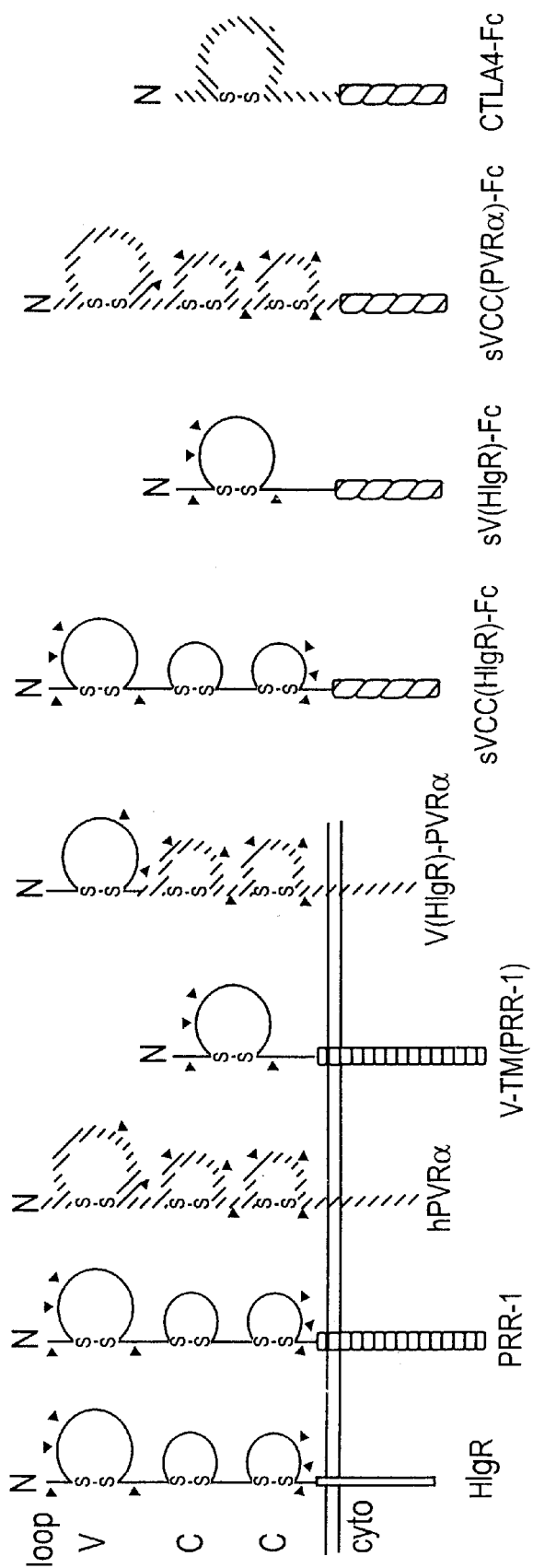

The present invention relates to HIgR (herpesviris immunoglobulin-like receptor) for the manufacture of medicaments for preventing or treating HSV-1, HSV-2 infections.

The present invention also relates to a novel immunoglobulin-like protein and medicaments which incorporate said antibodies and are useful in preventing or treating pathologies concerned with herpes simplex virus 1, herpes simplex virus 2 infections in humans. The invention also relates to methods for obtaining cell lines resistant to HSV-1, HSV-2 and BHV-1 infections and to cell lines expressing specific receptors which mediate entry of said virus within cellular environment to test efficacy of antiherpes drugs and antibodies, antiherpesvirus vaccines and herpesvirus-based vectors.

Alphaherpesviruses which includes HSV-1, HSV-2, PRV, and BHV-1, infect a variety of cells resulting in efficient virus production in a short replicative cycle. Infection in the mammals results in lesion of the mucocutaneous tissue, and specifically in humans produces lesion on the mucosal surfaces, with spread of virus to the nervous system and establishment of latent infections in neurons. Infections may lead in some cases, to encephalitis or meningitis, with an often fatal outcome.

The receptors which mediate herpes simplex virus (HSV) entry into cells have remained elusive for a long time for several reasons.

It has been known that binding of alphaherpesviruses to cells occurs through an interaction of virion glycoproteins gC with cell surface glycosaminoglycans, whereas the following entry of the capsid into the cytoplasm occurs via a fusion of the virion envelope with cell membrane. This last step involves at least the four glycoproteins gB, gD, and the heterodimer gH, gL.

Works of the past have allowed to ascertain that alphaherpesvirus gD is the virion component that interacts with a cell surface receptor. One cellular receptor which mediates virus entry was called herpesvirus entry mediator (HVEM), and has been redesignated HveA.

The molecular mechanisms underlying this process remain in part obscure, and a model is still lacking of how the interaction of gD with its cellular receptor triggers the fusion of the virion envelope with the plasma membrane and recruits the other virion glycoproteins. HveA, when transfected in cells which do not express any other suitable receptor, mediates HSV-1 entry, but has such a narrow distribution that its actual usage is limited to very specialized cell types, e.g. T-lymphocytes.

The general aim of the present invention is to provide new agents of interest in the medical field for preventing, treating the HSV infections.

One of the objects of the present invention is to provide prophilactic and therapeutic agents to HSV-1, HSV-2 by the identification of a region of HIgR/PRR1 that is functional in HSV-1 entry and interacts with HSV-1 gD. Another object is to provide an anti-HSV agent, or antibody, specifically designated to block HSV-1 infections.

Yet another object is to provide cells lines resistant to infection by HSV-1, HSV-2 and BHV-1 for the biotechnological identification and production of proteins which act as mediators of HSV in human or animal models.

A further object of the present invention is to provide cells line expressing HIgR and other HSV-1, HSV-2 mediators for testing the efficacy of antiherpes drugs, antibodies and protein which interfere with virus entry.

SUMMARY OF THE INVENTION

In accordance with a first aspect of the present invention, a novel member of the immunoglobulin superfamily named HIgR that confers susceptibility to HSV infection by mediating entry of the virus into cells and to sequences encoding this immunoglobulin superfamily member is provided. The present invention is based, in part, by the unexpected evidence that the N-terminal domain, called V-domain, is the region of the molecule functional in HSV-1 and HSV-2 entry into cells and in binding to the virion glycoprotein D. Included within the present invention is the application of this new immunoglobulin portion (peptide) and sequences in the medical field.

Applicants have now found, in accordance with a first aspect of the invention, a novel member of the Ig superfamily, hereinafter named HIgR, which acts as receptor for HSV-1 and HSV-2 entry into human cells.

The present invention further provides a monoclonal antibody which is able to bind HIgR and is able to block infection with HSV-1, HSV-2 and BHV into human cells or into cells expressing HIgR as a transgene for the manufacture of a medicament to prevent or treat HSV-1, HSV-2 and BHV infections.

In accordance with a preferred embodiment of the invention it is provided the use of the V domain or its derivatives for the manufacture of a medicament for preventing or treating HSV-1, HSV-2 and BHV infections.

In accordance with an embodiment of the invention it is also provided the specific use of monoclonal antibody R 1.302 to HIgR for the manufacture of a medicament for preventing or treating infections of human tissues by HSV-1, HSV-2 and cell-to-cell spread of said virus to neighboring cells such as hepidermic or nervous cells. The derivation of humanized antibodies for use in the medical field is also provided.

In particular, Applicants have found the new member of Ig superfamily named HIgR by the provision of herein below disclosed J1.1–2 cell line which is highly resistant to entry of HSV-1, -2, BHV-1 and which was selected by repeated exposures of BHKtk-cells to a recombinant HSV-1 expressing tumor necrosis factor 1 (TNF-α.). In accordance an embodiment of the invention, the screening of a human cDNA expression library for ones that restored susceptibility to J1.1–2 cells led to the isolation of a human cDNA one which encodes a novel transmembrane protein with features typical of the Ig superfamily and an overall molecular organization essentially overlapping that of the poliovirus receptor (PVR) (see Mendelsohn, C. L., E. Wimmer, and V. R. Racaniello. 1989. Cellular receptor for poliovirus: molecular cloning, nucleotide sequence, and expression of a new member of the immunoglobulin superfamily. Cell. 56:855–65), i.e. a V-like and two C-like domains bracketed by conserved cysteins. Applicants have now also found that the major region of HIgR/PRR1 with HSV-1 entry activity resides in the V domain. In particular, the V domain is a major determinant of HIgR/PRR1 in mediating HSV-1 entry and is sufficient to mediate HSV-1 entry into cells. Furthermore, the single V domain is sufficient for the in vitro physical interaction with gD in a specific manner. The analyses of the interaction of gD with the functional regions of its receptor lead to practical and industrial applications of the present invention.

Since it is instrumental to define the interaction between gD and HIgR/PRR1 in terms of minimal size of the functional domain, structural requirements, key residues, etc, in the present application, the major functional region of HIgR/PRR1 involved in and sufficient for HSV-1 entry and able to physically interact with the viral gD has been selected and acknowledged as being a region of about 114 as residues.

A novel class of anti-HSV agents/medicaments designed specifically to block HSV-1 infection in accordance with an aspect of the present invention is provided by the identification that a major functional domain of HIgR/PRR1 is encoded in the V domain, coupled with the demonstration that this domain is sufficient for physical binding to gD and to compete with virion infectivity. A further embodiment of the present invention provides for the construction of transgenic mice expressing HIgR, or HIgR and PRR-2, or HIgR and other mediators of HSV-1, HSV-2 and BHV-1 entry from transgenes, for the purposes of establishing a mouse model for efficacy studies of antiherpes drugs, antiherpes antibodies, antiherpes vaccines, antiherpes proteins which interfere with virus entry.

A further embodiment of the present invention provides for the construction of transgenic mice expressing HIgR, or HIgR and PRR-2, or HIgR and other mediators of HSV and BHV-1 entry from transgenes, for the purpose of establishing a mouse model system for efficacy studies of genetically engineered herpes simplex viruses to be employed as vectors against tumors of CNS.

A further embodiment of the present invention provides for the construction of transgenic mice expressing HIgR, or HIgR and PRR-2, or HIgR and other mediators of HSV and BHV-1 entry from transgenes, for the purpose of establishing a mouse model system for efficacy studies of genetically engineered herpes simplex viruses debilitated in virulence genes, to be employed as vaccines.

A further embodiment of the present invention provides for the construction of transgenic mice expressing HIgR, or HIgR and PRR-2, or HIgR and other mediators of HSV and BHV-1 entry from transgenes, for the purpose of establishing a mouse model system for efficacy studies of genetically engineered herpes simplex viruses for efficacy studies of substances that interfere with establishment of HSV latency and reactivation of HSV from latency.

A further embodiment of the present invention provides for the construction of transgenic mice expressing HIgR, or HIgR and PRR-2, or HIgR and other mediators of HSV and BHV-1 entry from transgenes, for the purpose of establishing a mouse model system that sustains BHV-1 infection, the mouse model system allowing to study the efficacy of drugs, antibodies and vaccines. In accordance to a further aspect of the present invention is provided a medicament which blocks HSV-1 and -2 infection in humans, and limits the virus-induced lesions. HSV-1 and -2 can infect as free virions or by cell-to-cell spread of virus. This lattern pathway of transmission of virus is particularly relevant in humans, as in humans HSV replicates in tissues of muco-epithelial origin, like oral and genital mucosae and corneal epithelia, and then spreads to nerve endings of sensory neurons. Upon reactivation from latency, the virus replicates in sensory neurons, and moves in retrograde direction to muco-cutaneous tissues. Therefore, HSV spread through human tissues is mainly by cell-to-cell transmission, a mechanism that greatly contributes to shielding the virus from the humoral immune response.

In particular, Applicants has found that HIgR, and/or its splice variant isoform HveC, are involved in cell to cell spread of HSV from cell to cell in cell cultures, and in human cell lines.

BRIEF DESCRIPTION OF THE DRAWINGS

FIG. 1. illustrates a comparative schematic representation of molecular structure of HIgR, PRR-1 and PVR. V and C domains formed by cysteine bonds typical of this cluster of Ig superfamily members are shown, along with the number of residues in each region. The regions differing between HIgR and PRR-1, i.e. transmembrane portion, the segment preceding it and cytoplasmic (cyto) tail are in solid black for HIgR and shaded for PRR-1.

Triangles indicate predicted N-glycosylation sites. Furthermore, HIgR, PRR1 and hPVRα represent the full-length molecules encoded by cDNAs. V-TM(PRR1) is an internally deleted version of PRR1, where the two C domains were deleted. V(HIgR)-PVRα is a chimeric protein formed of the V domain of HIgR fused to the CC domains, transmembrane and cytoplasmic region of hPVRα. sVCC(HIgR)-Fc, sV(HIgR)-Fc, sVCC(PVRα)-Fc, and CTLA4-Fc represent soluble forms of receptors constructed by fusion of the VCC or V domains of HIgR, or the V domain of CTLA4, with the Fc portion of human IgG1.

FIG. 2 shows a relative plating efficiency of HSV-1 and -2 strains in Vero, BHKtk- and the resistant J1.1–2 cells. Plaques in Vero and BHKtk-cells were scored by Giemsa staining, in J1.1–2 cells by immunostaining.

FIG. 3 shows the effect of HIgR expression on susceptibility of J1.1–2 cells to indicated HSV-1 and -2 strains. Gallery of representative micrographs of cells transfected with pcDNA3.1 vector alone (a), HIgR (b–d, f, h), or HveA(HVEM) (e, g, i). Infected cells were detected by immunostaining.

FIG. 4 illustrates the expression of HIgR and PRR-1 proteins in human cell lines. (A), FACS analysis of TF-1, IMR-32, Nalm-6 and U937 cells.

FIG. 5 shows the neutralization of R8102 Infectivity by MAb R1.321 to PRR-1. (A) Stable transformants of J1.1–2 cells expressing HIgR or PRR-1 in 96 wells were preincubated with indicated dilutions of IgGs from monoclonal antibody R1.302 to PRR-1, or from purified mouse IgGs for 2 h at 4° C. R8102 was added to the antibody-containing medium and allowed to absorb for further 90 min at 4° C. (B). Infectivity neutralization in HEp-2 and HeLa cells with MAb R1.302 ascites fluid, or unrelated monoclonal antibody. (C). Infectivity neutralization in TF-1 and 5637 cells with MAb R1.302, ascites fluid, or unrelated monoclonal antibody.

FIG. 6 shows the Northern blot analysis of HIgR+PRR-1 mRNA expression in human tissues. (A) Phosphoimages obtained with multiple tissue Northern blot membranes hybridized with the BamHI fragment of pLX1.12 containing the entire PRR-1 cDNA. The probe did not distinguish between HIgR and PRR-1 mRNAs. Two bands were detected, 2.4 and 1.8 kbp respectively. Note the highest level of expression in brain and spinal cord tissues. (B) Same membranes hybridized with β-actin probe.

Figures 7, 8:
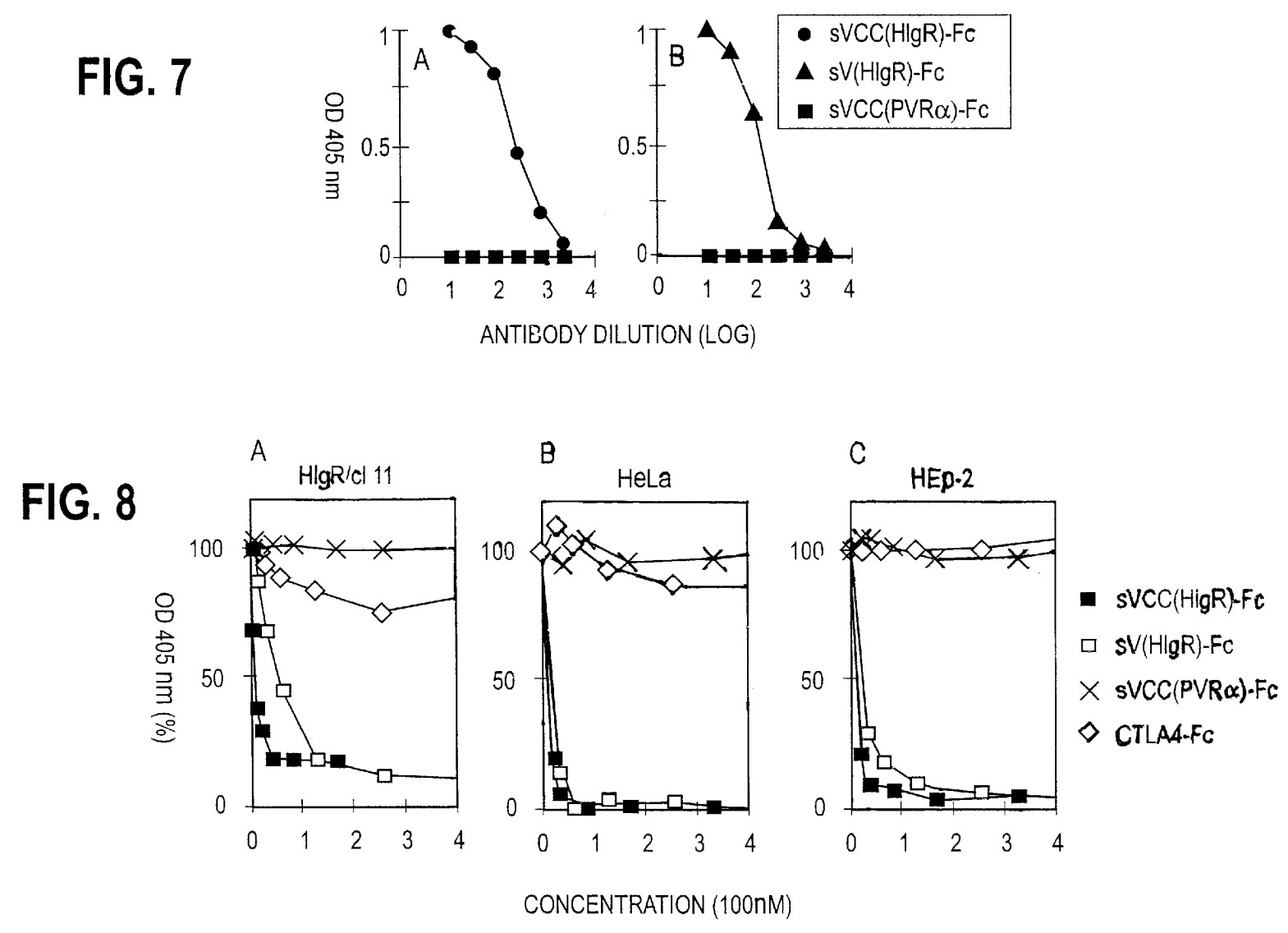

FIG. 7. A illustrates the binding of MAb R1.302 to the soluble form of HIgR -sVCC(HIgR)-Fc—containing the entire ectodomain (VCC) fused to Fc. B illustrates the mapping of the epitope recognized by the MAb R1.302 to the V domain of HIgR. sVCC(HIgR)-Fc, sV(HIgR)-Fc, or sVCC(PVRα)-Fc, immobilized to microwells through anti-human IgGs, were reacted with serial dilutions of biotinylated monoclonal antibody R1.302. Abscissa represents the monoclonal antibody dilutions (MAb Dil.) expressed as $Log_{10}$.

FIG. 8. Illustrates that HSV-1 infectivity is competitively blocked by the soluble forms of receptor, sVCC(HIgR)-Fc and sV(HIgR)-Fc, and not by sVCC(PVRα)-Fc or CTLA4-Fc. Replicate aliquots of R8102 were preincubated with the indicated amounts of sVCC(HIgR)-Fc, sV(HIgR)-Fc, sVCC (PVRα)-Fc, and CTLA4-Fc for 1 h at 37° C., and allowed to absorb to the HIgR-expressing cells HIgR/cl 11 (panel A), HeLa (panel B) or HEp-2 (panel C) cells for 2 h at 4° C. Infection was quantified at 16 h after infection as β-gal activity. Note that sVCC(PVRα)-Fc, closely related to HIgR, and CTLA4-Fc did not affect R8102 infectivity. Each point represents the average of triplicate assays. 100% indicates the optical density measured in untreated virus-infected cultures.

Figure 9:
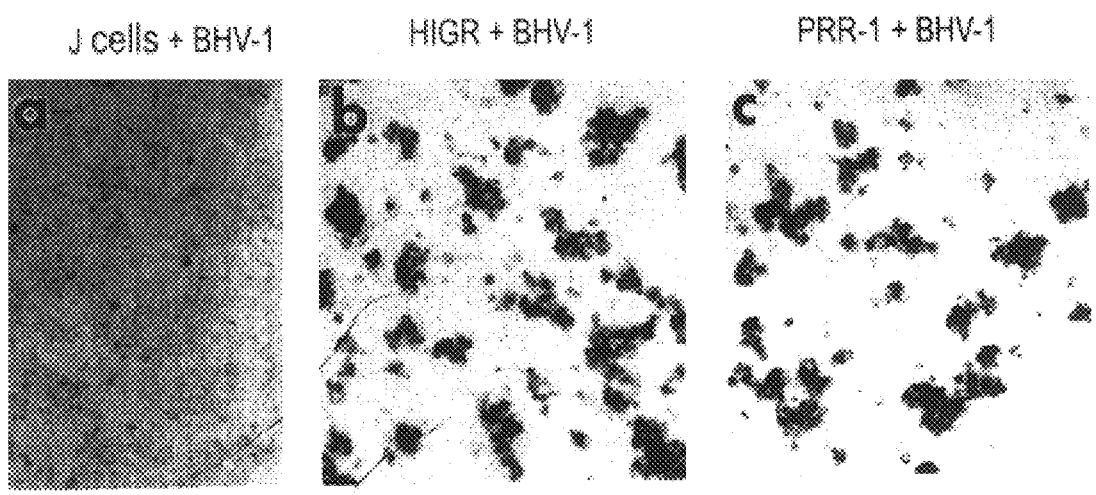

FIG. 9 illustrates the transfection of J1.1–2 cells with HIgR or PRR-1 confers susceptibility to BHV-1 infection. Micrographs of J1.1–2 cells transfected with pCF18 (HIgR) (b), pLX1.12 (PRR-1) (c), or pcDNA3.1 (a) infected with BHV-1, and immunostained with MAb 1240 to glycoprotein gB.

Figure 10:
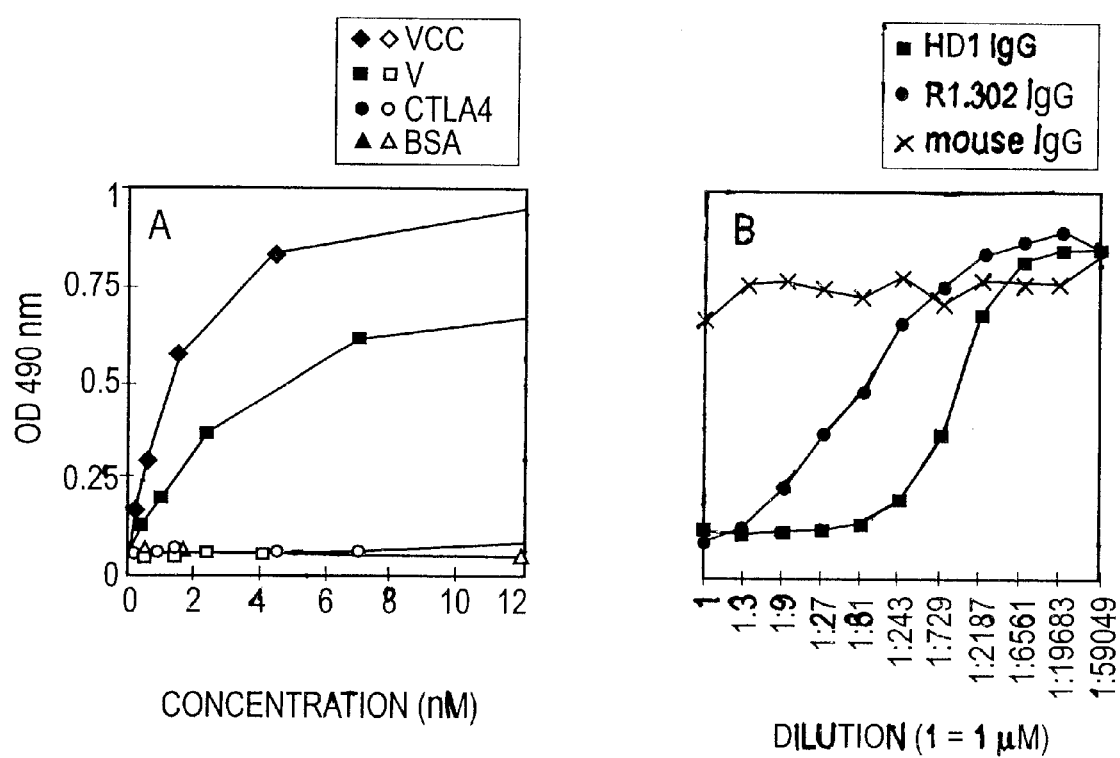

FIG. 10. A illustrates the in vitro binding of HSV gD to soluble forms of HIgR receptor sV(HIgR)-Fc, or sVCC (HIgR)-Fc or to CTLA4-Fc or BSA. gD (full symbols) or fetuin (open symbols) were immobilized to microwells, and then allowed to react with increasing concentrations of the indicated proteins. Binding was detected with anti-human IgG-peroxidase (1:6000).

FIG. 10B illustrates the competition of the in vitro binding of HSV gD to sV(HIgR)-Fc by monoclonal antibody R1.302 to PRR1, monoclonal antibodies to gD HD1, or purified mouse IgGs. A fixed amount of sV(HIgR)-Fc (10 nM), giving saturable binding to gD in panel A, was mixed with increasing amounts of IgGs from the indicated antibodies, and then allowed to react with gD, preimmobilized to microwells. Binding was revealed by incubation with anti-human IgG-peroxydase as above. Dilution 1 corresponds to 1 μM purified IgG for each antibody.

Figure 11A:
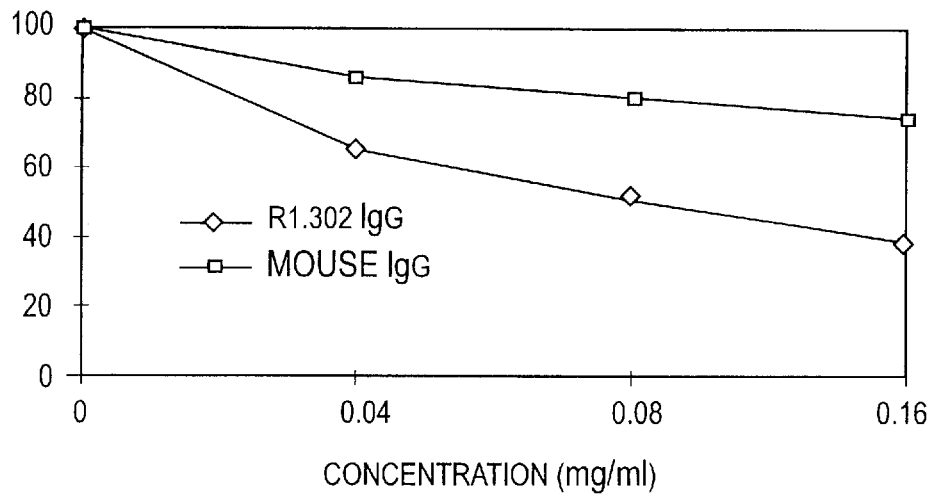
Figure 11B:
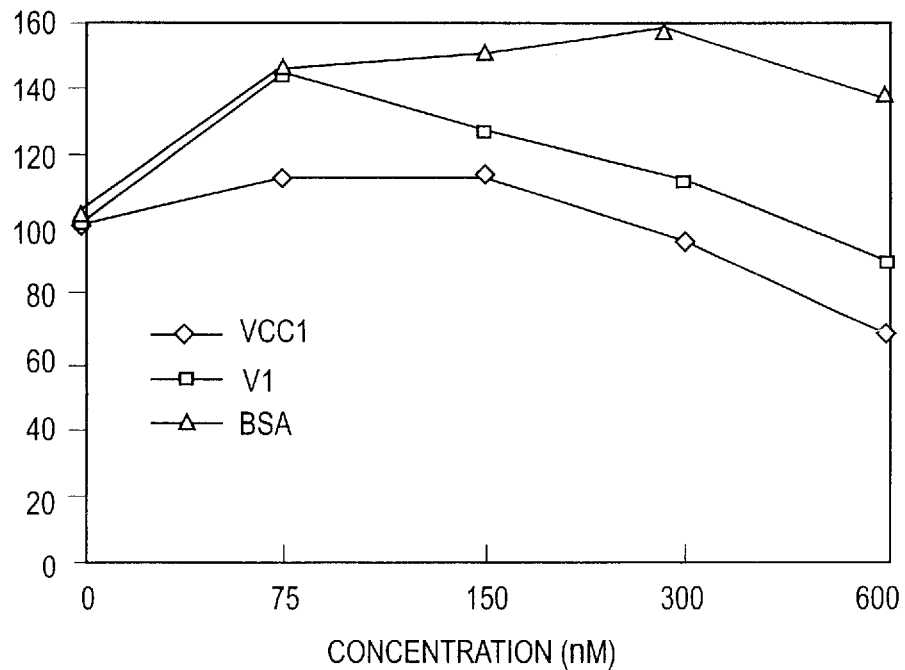

FIGS. 11a and 11b refer to MAb R1.302 and soluble HIgR inhibit plaque formation of R8102 in HIgR-expressing cells. In particular, FIG. 11a shows HIgR-expressing J cells in 96 wells, infected with R8102 were exposed to the indicated concentrations of MabR1.302 (♦), control mouse IgG (■), from 4 h after infection. Infection was detected 48 h later by permeabilization and quantitative detection of β-galactosidase activity with ONPG, followed by reading O.D. at 405 nm in a BIO-Rad ELISA reader. Each point represents the average of triplicate samples. 100% represents the optical reading in untreated cultures. FIG. 11b HIgR-expressing J cells infected with R8102 in 96 wells were exposed to the indicated concentration of soluble form of HIgR containing the entire ectodomain fused to Fc portion of human IgG (VCC1-Fc) (♦), or containing the single V domain (V1-Fc) (■), or to BSA (▼), from 4 h after infection. Infection was detected as in panel A. Each point represents the average of triplicate samples. 100% represents the optical reading in untreated cultures.

DESCRIPTION OF THE PREFERRED EMBODIMENT

The practice of the present invention will employ, unless otherwise indicated, conventional techniques of molecular biology, microbiology, recombinant DNA and immunology which are within the skill of the art. Such techniques are explained fully in the scientific literature.

Production of a Cell Line Resistant to HSV Infections

In accordance with an aspect of the invention BHKtk- cells have been exposed to recombinant HSV R8996 which secretes TNF-α in the medium. The few cells surviving a 10 PFU/cell infection were grown and infected for two more times with the same virus at 100 PFU/cell. Some cells in the culture showed a persistent cytopathic effect which was eliminated by cultivation of the cells for 20 days in the presence of HD-1 (ascites fluid 1:250), a potent neutralizing monoclonal antibody to gD (see Pereira, L., T. Klassen, and J. R. Baringer. 1980. Type-common and type-specific monoclonal antibody to herpes simplex virus type 1. Infect Immun. 29:724–32) and for additional 20 days in the presence of a mixture of HD-1 and 52S (see Showalter, S. D., M. Zweig, and B. Hampar. 1981. Monoclonal antibodies to herpes simplex virus type 1 proteins, including the immediate-early protein ICP 4. Infect Immun. 34:684–92), a neutralizing antibody to gH. The cells were cloned by single cell plating with medium supplemented with 20% fetal calf serum and 20% conditioned medium from BHKtk- cells. Twelve clones were assayed for resistance to infection with R8102, which carries a LacZ gene fused to α-$^{27}$, and X-gal staining monitored infection. All clones were resistant to infection. In clone J1.1–2, no more than an average of 10 cells per monolayer ($3 \times 10^6$ cells) exhibited evidence of infection after exposure to 5 PFU/cell The J1.1–2 cells have been propagated for at least eight months without change in phenotype.

The resistance in clone J1.1–2 has been ascertained to be at the entry level since in HSV-infected cells, a gene expression does not require prior viral protein synthesis and in R8102 the LacZ gene was driven by the α27 promoter. Thus, lack of LacZ expression indicated that the block to infection with R8102 in J1.1–2 cells preceded a gene expression. Additional evidence that block is at the entry level was as follows: (α) At 4° C. HSV attaches, but does not penetrate cells. We compared the extent of virus attachment to J1.1–2 and BHKtk- cells by measuring the virus remaining unattached after 120 min of absorption at 4° C., and found no difference (b) In the second experiment, J1.1–2 cells were transfected with the mediator of HSV entry HVEM(HveA), and infected with R8102. The cells became infectable. The following materials and methods have been used in the methodology disclosed in the following examples which are illustrative of a first general aspect of the present invention.

Cells, Viruses and Plasmids

All cells were grown in Dulbecco's modified Eagle medium (DME) supplemented with 5% fetal calf serum. The wild type viruses HSV-1(F), HSV-2(G) and HSV-1(MP) were described in Hill, T. J., H. J. Field, and W. A. Blyth. 1975. Acute and recurrent infection with herpes simplex virus in the mouse: a model for studying latency and recurrent disease. J Gen Virol. 28:341–53; Schröder, C. H., B. Stegmann, H. F. Lauppe, and H. C. Kaerner. 1975. An unusual defective genotype derived from herpes simplex virus strain ANG. Intervirology. 6:270–84 and Wildy, P., W. C. Russel, and R. W. Horne. 1960. The morphology of Herpes virus. Virology. 12:204–22 . HSV (Sc-16, ANG, KOS, and HFEM) BHV-1 and PRV were disclosed in Hill, T. J., H. J. Field, and W. A. Blyth. 1975. U21, U10, and U30 carry mutations in gD gene which overcome gD-mediated block to infection as disclosed in Brandimarti, R., T. Huang, B. Roizman, and G. Campadelli Fiume. 1994. Mapping of herpes simplex virus 1 genes with mutations which overcome host restrictions to infection. Proc Natl Acad Sci USA. 91:5406–10 and Campadelli-Fiume, G., S. Qi, E. Avitabile, L. Foà-Tomasi, R. Brandimarti, and B. Roizman. 1990. Glycoprotein D of herpes simplex virus encodes a domain which precludes penetration of cells expressing the glycoprotein by superinfecting herpes simplex virus. J Virol. 64:6070–9. R8996, a recombinant carrying a TNF-α gene under the control of the epidermal growth factor receptor I promoter in place of the α₁34.5 gene and R8102, a recombinant carrying a LacZ gene fused to α27 and inserted between $U_L3$ and $U_L4$ genes were gifts of B. Roizman and will be reported elsewhere. Viruses were grown and titrated by plaque assay in Vero cells. Infectivity of R8102 was assayed by light microscopy of cells expressing β-galactosidase (β-gal) as disclosed in Montgomery, R. I., M. S. Warner, B. J. Lum, and P. G. Spear. 1996. Herpes simplex virus-1 entry into cells mediated by a novel member of the TNF/NGF receptor family. Cell. 87:427–36. Cells expressing PRR-1 were obtained by transfection of pLX1.12 containing PRR-1 cDNA cloned in the BamHI site of pLXSN. Stable transformants of J1.1–2 cells expressing HIgR or PRR-1 were obtained by G418 neomycin selection of pCF18- or pLX1.12-transfected cells.

Antibodies. HD-1 (anti-gD, Goodwin Institute, Plantation Fla.) (37), 52S (anti-gH, ATCC) (see Showalter, S. D., M. Zweig, and B. Hampar. 1981. Monoclonal antibodies to herpes simplex virus type 1 proteins, including the immediate-early protein ICP 4. Infect Immun. 34:684–92) were used for J1.1–2 cell derivation, LP1 (anti-αTIF) (30), rabbit anti-gM (see Baines, J. D., and B. Roizman. 1993. The UL10 gene of herpes simplex virus 1 encodes a novel viral glycoprotein, gM, which is present in the virion and in the plasma membrane of infected cells. J Virol. 67:1441–52), 1240 to BHV-1 gB for immunostaining of infected cells, monoclonal antibody R1.302 to PRR-1 (see Lopez, M., F. Jordier, F. Bardin, L. Coulombel, C. Chabannon, and P. Dubreuil. 1997. CD155 Workshop: Identification of a new class of IgG superfamily antigens expressed in hemopoiesis., p. 1081–3. Leukocyte Typing VI, White cells differentiation antigens) to detect expression of HIgR and PRR-1 proteins and for infectivity neutralization assays. Alkaline phosphatase-anti-rabbit and biotin-avidin anti-mouse antibodies (ABC-Kit) were from Sigma and Vector Laboratories.

Method of Selection of a Human cDNA Clone that Confers Susceptibility to J1.1–2

J1.1–2 cells were transfected with DNA pools from a HeLa cDNA library, exposed to R8102 30 h after transfection and monitored for a-galactosidase activity. The following method led to the selection of clone pCF18, which conferred susceptibility to all the transfected cells in the culture.

Method of isolation of HIgR cDNA

Screening of a HeLa cDNA library cloned unidirectionally in pcDNA3.1 (Invitrogen) was done as described in Montgomery, R. I., M. S. Warner, B. J. Lum, and P. G. Spear. 1996. Herpes simplex virus-1 entry into cells mediated by a novel member of the TNF/NGF receptor family. Cell. 87:427–36. In accordance with this method, the library was plated onto 100 plates, colonies were grown, harvested and pooled into groups of 10 plates each. The pools were grown in liquid broth. Plasmid DNA was extracted and purified with Qiagen columns (M-Medical, Florence). J1.1–2 cells in 25 cm² flasks were transfected by means of LipofectAMINE (Gibco Laboratories, Milano) (2.5 μg DNA in 20 μl of LipofectAMINE). At 30 h they were exposed to R8102 (5 PFU/cell) for 16 h, and assayed for β-galactosidase. In each experiment, replicate cultures were transfected with a plasmid carrying LacZ gene cloned in pcDNA3.1, or with pBEC10 (HveA) followed by infection with R8102 and X-gal staining. The cDNA pools that yielded the highest number of infected cells were subjected to repeated subdivisions. The final plasmid pCF18 was sequenced by Primm, (Department of Biological and Technological Research, San Raffaele Biomedical Scientific Park, Milano).

Methodology for Immunofluorescence and FACS Analysis

For immunofluorescence, cells grown in glass coverslips were fixed with acetone, and reacted with MAb R1.302 (1:100) followed by biotinylated anti-mouse antibodies (Vectastain ABC Kit) and Extravidin-TRITC (Sigma). FACS analysis was performed as described in Lopez, M., F. Jordier, F. Bardin, L. Coulombel, C. Chabannon, and P. Dubreuil. 1997. CD155 Workshop: Identification of a new class of IgG superfamily antigens expressed in hemopoiesis., p. 1081–3. Leukocyte Typing VI, White cells differentiation antigens, and analyzed in a FACSscan flow cytometer.

Infectivity neutralization assays.

Cells grown in 96 well trays were preincubated with the indicated amounts of antibodies, either purified IgGs or ascites fluid, in 25 μl of medium for 2 h at 4° C. The appropriate amount of R8102 in 7.5 μl was then added for further 90 min at 4° C. Viral inoculum was removed, cells were rinsed two times, overlaid with medium containing the same concentration of antibodies as present during the preabsorption, shifted to 37° C. and incubated for 16 h. galactosidase activity was assayed as described in Montgomery, R. I., M. S. Warner, B. J. Lum, and P. G. Spear. 1996. Herpes simplex virus-1 entry into cells mediated by a novel member of the TNF/NGF receptor family. Cell. 87:427–36. Optical density was read in a BioRad ELISA reader. For each antibody concentration triplicates were run. Data represent the average of at least two experiments. 100% value represents data obtained with infected cells not exposed to antibodies. Infectivity neutralization was detected irrespective of whether purified IgGs or ascites fluids were employed.

Northern blot analysis.

Human multiple tissue Northern (MTN™) membranes from Clontech were hybridized with BamHI fragment from pLX1.12 labeled with ³²P dCTP, according to manufacturer instructions. The membranes were also probed with a β-actin probe to verify hybridation conditions.

Description of HIgR encoded in pCF18.

The approximately 2500 bp insert in pCF18 contained an ORF predicted to encode a 458 amino acid protein (designated HIgR) with a 50.7 kDa mass according to SEQ ID NO:1 (see sequence listing). This is a novel protein that, as such, was never disclosed before in the literature. The predicted protein had structural elements typical of type 1 membrane-bound proteins, a N-terminal signal sequence with cleavage at Ser30, and a hydrophobic transmembrane region at residues 346–369. The ectodomain carried, in addition to seven potential N-glycosylation sites, six cysteine residues and consensus Ig motifs which identified three domains, one V-like and two C-like, 72, 53, 46 residues, respectively (SEQ ID NO:1) (for a representation of the predicted structure, see FIG. 1). These features defined the protein encoded by pCF18 as belonging to the Ig superfamily. The sequence was identical up to nt 1002 to that of poliovirus related-receptor 1 (PRR-1) cDNA, (see Lopez, M., F. Eberle, M. G. Mattei, J. Gabert, F. Birg, F. Bardin, C. Maroc, and P. Dubreuil. 1995. Complementary DNA characterization and chromosomal localization of a human gene related to the poliovirus receptor-encoding gene. Gene. 155:261–5), except for absence of three non consecutive cytosines, which modified the aa sequence between residues 194 and 204 (SEQ ID NO:1). Divergence between HIgR and PRR-1 started at nt 1002 immediately after a splice donor consensus sequence. As alternative splicing is very frequent among Ig superfamily transcripts, e.g. in poliovirus receptor (PVR) (see Koike, S., H. Horie, I. Ise, A. Okitsu, M. Yoshida, N. Iizuka, K. Takeuchi, T. Takegami, and A. Nomoto. 1990. The poliovirus receptor protein is produced both as membrane-bound and secreted forms. Embo J. 9:3217–24) and PRR-2 (see Eberlé, F., P. Dubreuil, M. G. Mattei, E. Devilard, and M. Lopez. 1995. The human PRR2 gene, related to the human poliovirus receptor gene (PVR), is the true homolog of the murine MPH gene. Gene. 159:267–72) it seems highly probable that the cDNA encoded by pCF18 represents a previously unknown, alternative splice variant of PRR-1. HIgR has a shorter C-terminal cytoplasmic tail than PRR-1 (SEQ ID NO:1 and FIG. 1), a situation similar to that of PRR-2α and δ (see Eberlé, F., P. Dubreuil, M. G. Mattei, E. Devilard, and M. Lopez. 1995. The human PRR2 gene, related to the human poliovirus receptor gene (PVR), is the true homolog of the murine MPH gene. Gene. 159:267–72). In vitro transcription-translation of pCF18 yielded a protein with an apparent mass of 57 kDa which increased to 70 kDA in the presence of microsomes, and showed discrete intermediate bands, consistent with glycosylation of some of the predicted sites.

HIgR confers susceptibility to a wide range of HSV-1 and -2 strains.

Figure 2:
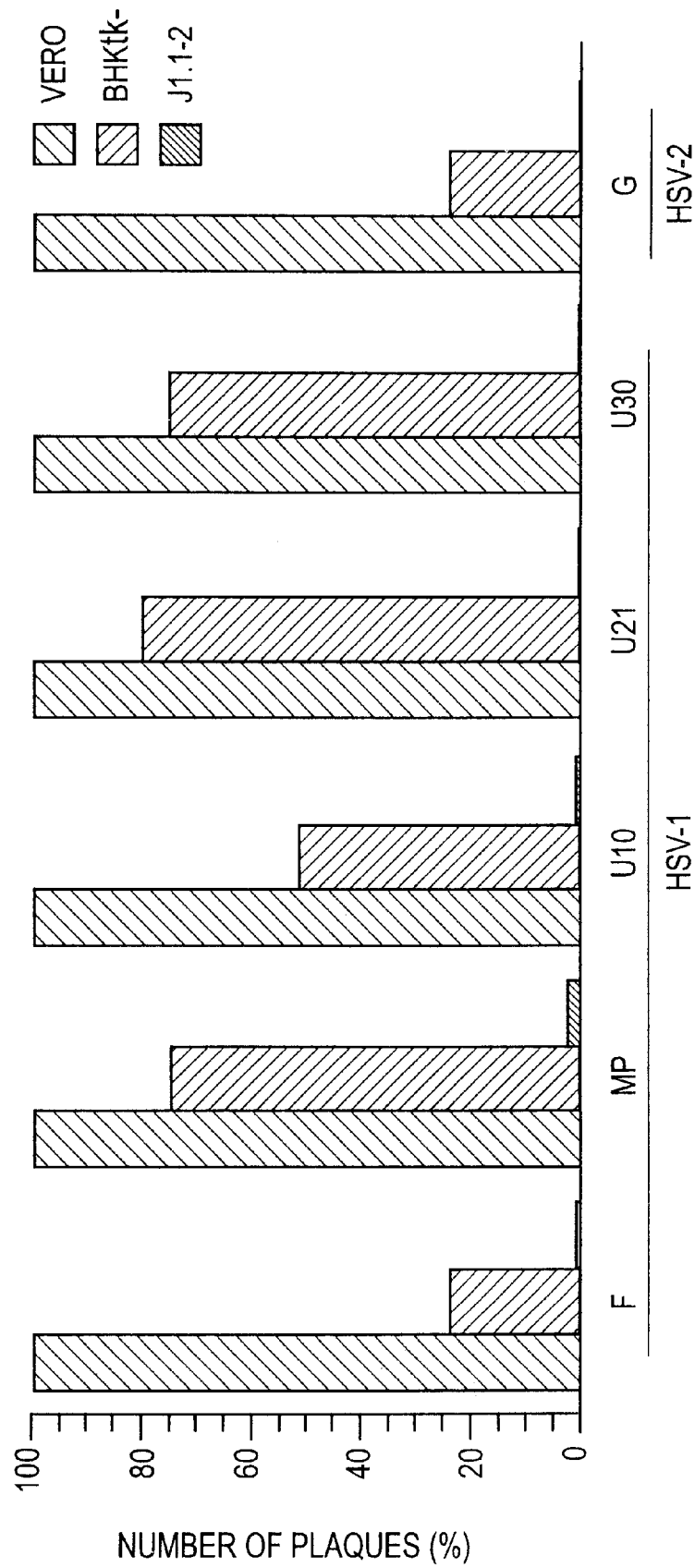

Experiments established that J1.1–2 cells were simultaneously resistant to all HSV-1 and HSV-2 strains tested (as shown in FIG. 2). These included the wild type strains HSV-1(F), (KOS), (SC-16), and HSV-2(G), two syncytial strains HSV-1(MP) and HSV-1(HFEM) with mutations in gK (see Pogue-Geile, K. L., and P. G. Spear. 1987. The single base pair substitution responsible for the Syn phenotype of herpes simplex virus type 1, strain MP. Virology. 157:67–74) and gB (see De Luca, N., D. J. Bzik, V. C. Bond, S. Person, and W. Snipes. 1982. Nucleotide sequences of herpes simplex virus type 1 (HSV-1) affecting virus entry, cell fusion, and production of glycoprotein gB (VP7). Virology. 122:411–23 and Ruyechan, W. T., L. S. Morse, D. M. Knipe, and B. Roizman. 1979. Molecular genetics of herpes simplex virus II. Mapping of the major viral glycoproteins and of the genetic loci specifying the social behavior of infected cells. J Virol. 29:677–97) which induce polykaryocyte formation of infected cells, four strains with mutations in gD which overcome gD-mediated block to infection, three of which—U21, U30, U10-selected in our laboratory (see Brandimarti, R., T. Huang, B. Roizman, and G. Campadelli Fiume. 1994. Mapping of herpes simplex virus 1 genes with mutations which overcome host restrictions to infection. Proc Natl Acad Sci USA. 91:5406–10 and Campadelli-Fiume, G., S. Qi, E. Avitabile, L. Foà-Tomasi, R. Brandimarti, and B. Roizman. 1990. Glycoprotein D of herpes simplex virus encodes a domain which precludes penetration of cells expressing the glycoprotein by superinfecting herpes simplex virus. J Virol. 64:6070–9) and ANG, a clinical isolate (see Dean, H. J., S. S. Terhune, M. T. Shieh, N. Susmarski, and P. G. Spear. 1994. Single amino acid substitutions in gD of herpes simplex virus 1 confer resistance to gD-mediated interference and cause cell-type-dependent alterations in infectivity. Virology. 199:67–80 and also Schröder, C. H., B. Stegmann, H. F. Lauppe, and H. C. Kaerner. 1975. An unusual defective genotype derived from herpes simplex virus strain ANG. Intervirology. 6:270–84).

Lack of plaque formation (FIG. 2, in which it is illustrated relative plating efficiency of HSV-1 and HSV-2 strains in Vero, BHKtk-, and J 1.1–2 cells. Plaques in Vero and BHKtk- cells were scored by Giemsa staining and those in J1.1–2 cells were scored by immunostaining), or immunostaining of monolayers assessed resistance to infection.

Figure 3:
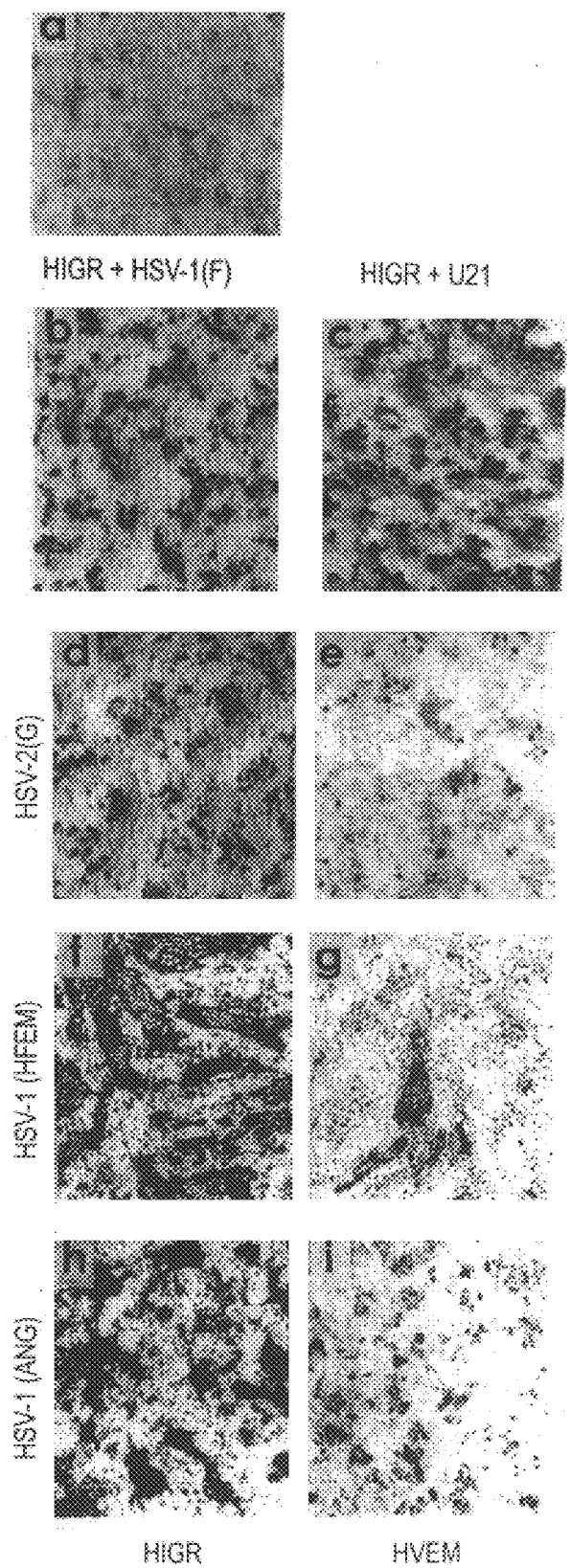

To determine the range of HSV strains to which HIgR conferred susceptibility, J1.1–2 cells transfected with pCF18, or pcDNA3.1 vector, were exposed to the above virus strains. Infected cells were readily detected with each virus tested (in accordance with FIG. 3). Cells infected with aggregating strains were single or formed small aggregates. Cells infected with syncytial strains HSV-1(MP), (HFEM) and (ANG) formed syncytial plaques. The characteristic of J1.1–2 cells resistant to a wide range of HSV strains differentiates J1.1–2 from CHO cells, which show moderate resistance to HSV-2 and to the syncytial strain MP. Furthermore, transfection of CHO cells with HveA increased susceptibility to HSV-2 and to syncytial strain MP to a low level, and had almost no effect on HSV gD mutants able to overcome the gD-mediated block (see Montgomery, R. I., M. S. Warner, B. J. Lum, and P. G. Spear. 1996. Herpes simplex virus-1 entry into cells mediated by a novel member of the TNF/NGF receptor family. Cell. 87:427–36). By contrast with HveA, transfection of J1.1–2 cells with HIgR conferred high sensitivity to all HSV-1 and -2 strains tested. We also noticed that HIgR was much more efficient than HveA(HVEM) in conferring susceptibility to J1.1–2 cells to infection with HSV-2 and syncytial strains MP, HFEM, and ANG.

Transfection with HIgR or PRR-1 confers susceptibility to BHV-1.

J1.1–2 cells were not susceptible to BHV-1 infection. Susceptibility was restored by transfection with HIgR or PRR-1 (in accordance with FIG. 9). Surprisingly, J1.1–2 cells were susceptible to PRV infection; hence the effect of HIgR expression on this virus is not investigated. With respect to BHV-1, the results indicate that although HIgR and PRR-1 do not represent the natural receptors employed by BHV-1 in bovine cells and in its natural host, the human HIgR or PRR-1 can be used promiscuously by the bovine herpesvirus, to achieve entry into cells. With respect to PRV, the results indicate that this virus finds in J1.1–2 cells a receptor, which can not be utilized by HSV-1 and -2 or BHV-1.

Distribution of HIgR or PRR-1 Proteins in Human Cell Lines.

To ascertain if HIgR or PRR-1 are the authentic receptors employed by HSV in human cell lines, it has been detected expression of these molecules at the protein level.

Figure 4:
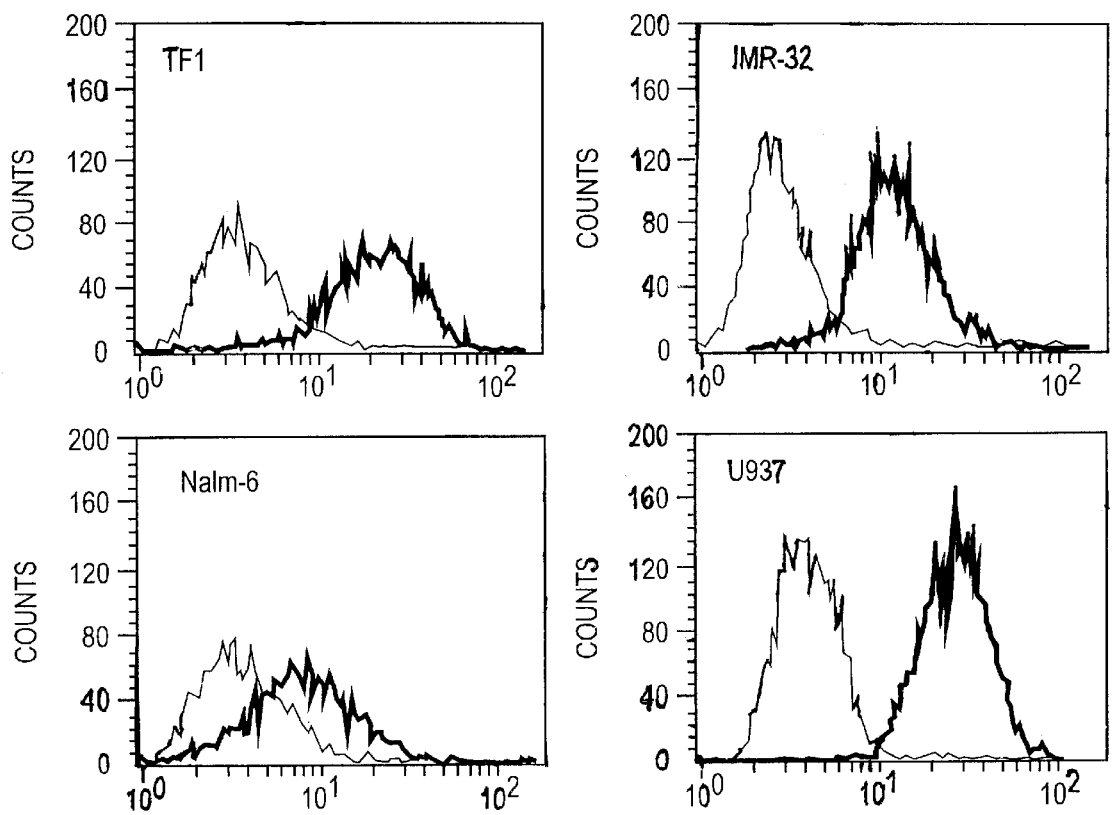

A monoclonal antibody to PRR-1, designated as MAb R1.302 (see Lopez, M., F. Jordier, F. Bardin, L. Coulombel, C. Chabannon, and P. Dubreuil. 1997. CD155 Workshop: Identification of a new class of IgG superfamily antigens expressed in hemopoiesis., p. 1081–3. Leukocyte Typing VI, White cells differentiation antigens) has been used. As MAb R1.302 reacted to cells expressing HIgR (not shown), the epitope recognized by MAb R1.302 must reside in the ectodomain of the molecule. The distribution of HIgR and/or PRR-1 protein was next investigated by flow cytometry or by indirect immunofluorescence and found to be positive on numerous human cell lines, HEp-2, HeLa (both carcinoma, epithelial), TF-1 (hematopoietic progenitor), IMR-32 and Lan5 (both neuroblastomaα), Nalm-6 (lymphoid, precursor-B), 5637 and T24 (bladder carcinoma, epithelial) (as shown in FIG. 4) referring to expression of HIgR and PRR-1 in human cell lines and specifically, to FACS analysis of TF-1, IMR-32, Nalm-6 and U937 cells. Previously, reactivity to MAb R1.302 was detected in additional human cells lines, including U937 (myeloid) (see FIG. 9), Burkitt's lymphoma Raji and Daudi, RPMI 8866 and 0467 (B-cells), RPMI 8266 and U266 plasmacytoid), CEM (T-cells) (see Lopez et al. previously cited). Altogether these data indicate that HIgR and PRR-1 proteins are widely represented in human cell cultures of different lineages, including epidermal, neuronal, myeloid and lymphoid.

Neutralization of HSV infectivity mediated by HIgR and PRR-1 by anti-PRR-1 Antibody.

Figure 5:
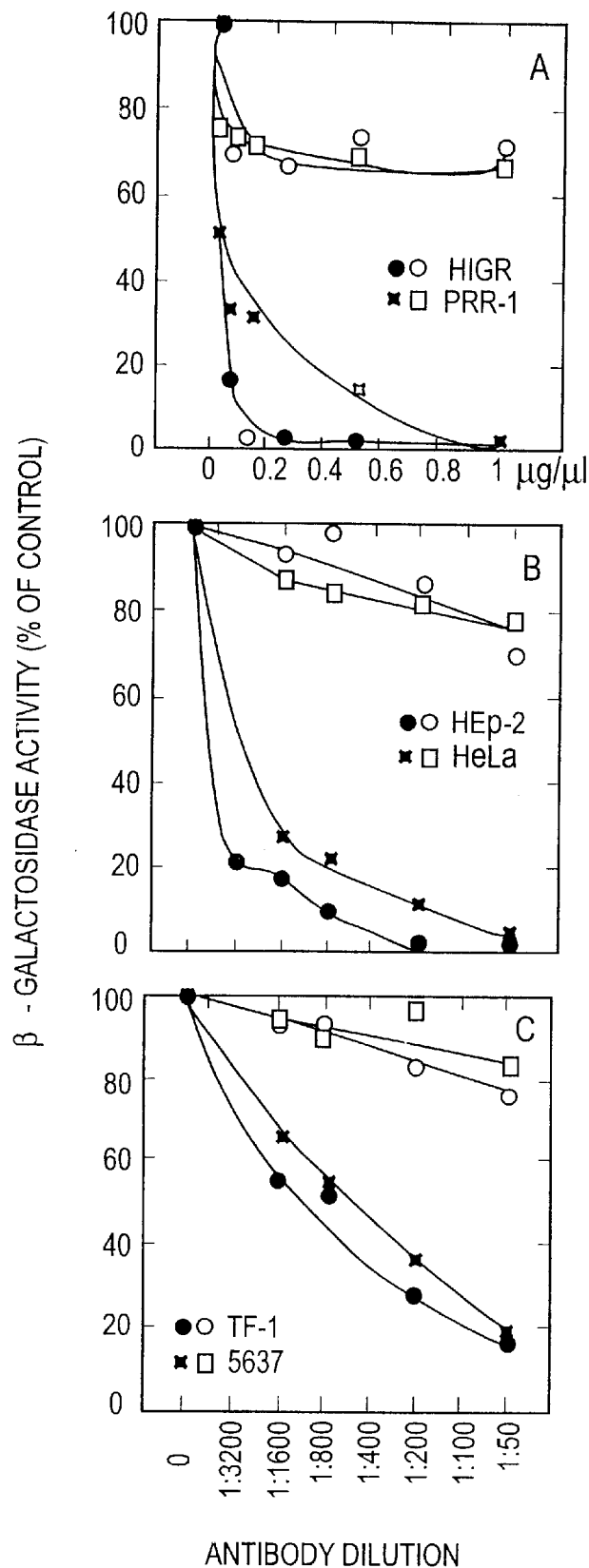

In J1.1–2 cells stably transformed with pCF18 (HIgR) or pLX1.12 (PRR-1), exposure to increase concentrations of MAb R1.302 prior to infection inhibited R8102 infectivity in a dose-dependent manner (FIG. 5). Mouse IgGs had only a low inhibitory effect. To ascertain if the HIgR molecule detected in human cell lines is actually employed as receptor by HSV, Applicants carried out infectivity neutralization experiments on representative cell lines. The results in FIG. 10B and C show that in HEp-2, HeLa, TF-1, and 5637 cells HSV infectivity was reduced in a dose-dependent fashion by MAb R1.302, while an unrelated monoclonal antibody had only minimal effects. From these data infer three conclusions were inferred. First, the experiment provides compelling evidence that susceptibility to infection in HIgR- and PRR-1-expressing J1.1–2 cells is dependent upon a direct interaction of virions with these molecules. Second, infectivity neutralization in human cell lines coupled with protein expression demonstrates that these molecules are actually utilized as receptors for HSV entry. Third, as the portion of molecule shared by HIgR and PRR-1 is the ectodomain (see FIG. 2), the functional domain of HIgR or PRR-1 to mediate HSV entry maps to the ectodomain of the molecules.

Distribution of HIgR or PRR-1 mRNAs in human tissues.

Figure 6:
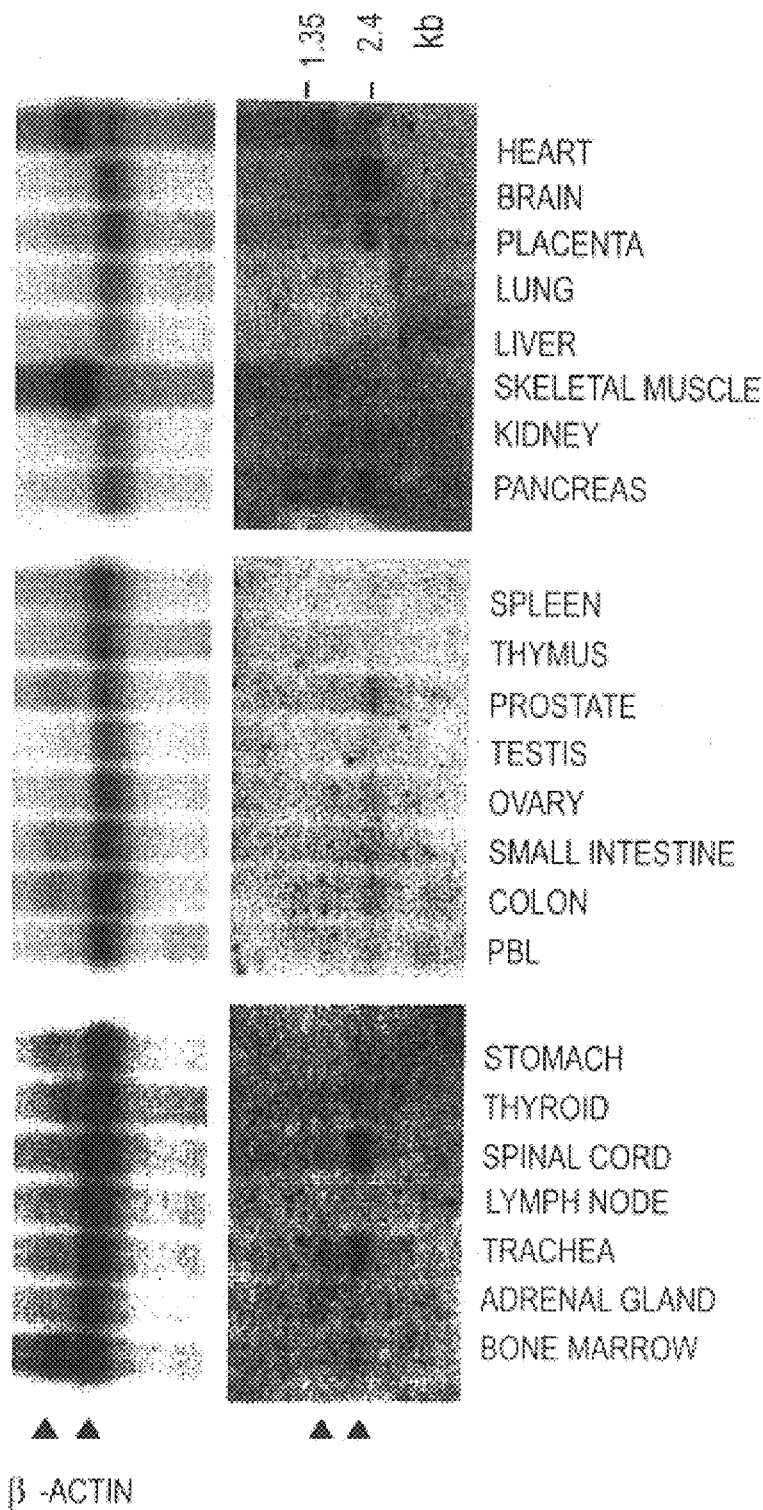

The expression of HIgR and/or PRR-1 in human tissues was assessed by Northern blot analysis carried out on human multiple tissue Northern blot membranes from Clontech. The probe consisted of the BamHI fragment of pLX1.12 comprising the entire PRR-1 cDNA, and hybridized to both HIgR and PRR-1 mRNAs. The results in FIG. 6 show that two bands 2.4 and 1.8 kbp, respectively were detectable in several tissues. The highest level of expression was detected in samples from nervous tissue, brain and spinal cord, followed by trachea, prostate and pancreas.

Cells expressing HIgR bind gD.

J1.1–2 cells transfected with pCF18, or pcDNA3.1, were reacted with a biotinylated recombinant soluble form of gD [gD-1(Δ290–299t)] (see Nicola, A. V., S. H. Willis, N. N. Naidoo, R. J. Eisenberg, and G. H. Cohen. 1996. Structure-function analysis of soluble forms of herpes simplex virus glycoprotein D. J Virol. 70:3815–22), followed by TRITC-conjugated Extravidin. The results in FIG. 12b, c show that a portion of the cells in the culture bound gD, based on fluorescence labeling. The number of labeled cells was consistent with a transient expression assay. Fluorescence localized mainly to vesicles in the cytoplasm, as expected for a membrane-bound protein. Cells transfected with plasmid alone or pCF18-transfected cells treated with Extravidin in the absence of gD (not shown), were not labeled. Overlapping results were obtained in pLX1.12-transfected J1.1–2 cells (data not shown).

It has been found that the relevant properties of HIgR as mediator of HSV entry into human cells are as follows:

(i) HIgR enable entry of all wild type and mutant HSV-1 and -2 strains tested, including mutants which induce the fusion of cells, and mutants which overcome the gD-mediated restriction to infection. This property differentiates HIgR (see Geraghty, R. J., C. Krummenacher, G. H. Cohen, R. J. Eisenberg, and P. G. Spear. 1998. Entry of alphaherpesviruses mediated by poliovirus receptor-related protein 1 and poliovirus receptor. Science. 280:1618–20) from HveA, which shows a narrower viral spectrum (see Montgomery, R. I., M. S. Warner, B. J. Lum, and P. G. Spear. 1996. Herpes simplex virus-1 entry into cells mediated by a novel member of the TNF/NGF receptor family. Cell. 87:427–36).

(ii) HIgR enables HSV entry into J1.1–2 cells independently of HveA.

(iii) Cells expressing HIgR bind gD, as expected from numerous studies pointing to gD as the virion component engaged in virus entry through interaction with cellular receptor molecules.

(iv) HIgR isoforms are highly distributed among human cell lines susceptible to HVS infection and commonly used for HSV studies, like HEp-2, HeLa, human fibroblasts, U937, and numerous other human cell lines of different origin, like IMR-32 and Lan5 (neuroblastoma), TF-1 (hematopoietic progenitor), 5637 and T24 (bladder carcinoma), Nalm-6 (lymphoid, precursor B), as well as in plasmacytoid cells and T-lymphocytes Lopez, M., F. Jordier, F. Bardin, L. Coulombel, C. Chabannon, and P. Dubreuil. 1997. CD155 Workshop: Identification of a new class of IgG superfamily antigens expressed in hemopoiesis., p. 1081–3. Leukocyte Typing VI, White cells differentiation antigens), mRNA analysis showed that some of these cell lines express either one or the other of the two isoforms, while some express both.

(v) A monoclonal antibody to PRR-1 neutralizes HSV-1 infectivity in HIgR- or PRR-1-transformed cells as well as in human cell lines. This provides unambiguous evidence of the actual usage of these molecules as HSV-1 receptors in human cell lines. It also shows that viral entry mediated by HIgR occurs through a direct interaction of the receptor molecules with virions.

(vi) HIgR mRNA is expressed in human tissues, the highest level of expression being detected in samples from the nervous system.

HIgR adds a novel member to the cluster of Ig homologs, which includes PVR, hPRR-1, hPRR-2α and δ and homologous proteins of simian, murine and rat origin. They share three characteristics:—a common molecular structure defined by the six conserved cysteines (FIG. 3A), —ability to originate multiple isoforms by alternative splicing, —ability of the human members to mediate the entry of some alphaherpesviruses.

Here it is shown that HIgR and PRR-1 fulfill criteria that allow them to be considered as bonafide receptors for HSV-1 and HSV-2. First, these proteins are present in a variety of human cells susceptible to HSV infection, as detected by reactivity with monoclonal antibody. Second, the neutralizing activity of the antibody in the same cells which express the HIgR or PRR-1 proteins provides unambiguous evidence for the actual usage of these receptors in human cell lines. Third, as the virus must infect neurons in order to establish latency, the finding that mRNAs for HIgR or PRR-1 are expressed in human tissues, with the highest expression being detected in nervous system samples, makes infection in humans feasible.

Current work provides evidence that the region of HigR/PRR-1 which mediates entry is located in the V domain by mapping to the ectodomain of HIgR/PRR-1 the functional domain mediating alphaherpesviruses entry into cells, by showing the actual distribution of HIgR/PRR-1 at the protein level in human cell cultures, by providing evidence for actual usage of the receptors in these same cells, and by indicating possible usage of receptors in humans in the path of neurons infection by HSV. Some aspects of the present invention are better illustrated by reference to the following non-limiting examples.

The following materials and methods have been used in the methodology disclosed in Examples 1–4.

Cells and viruses. Cells were grown in Dulbecco's modified Eagle medium (DME) supplemented with 5% fetal calf serum. HIgR/cl 11, PRR1/cl 5 and V-TM(PRR1)/Q were obtained by lipofectamine transfection of J1.1–2 cells (see Cocchi, F., Menotti, L., Mirandola, P. & Campadelli-Fiume, G. (1998) J Virol In press) with pCF18 (HIgR), pLX1.12 (PRR1), or pCDTMR1V.3 and neomicin G418 selection. The HSV-1 recombinant R8102 carries the LacZ gene under the control of the α27 promoter inserted between $U_L3$ and $U^L4$ genes, was a gift of B. Roizman, and will be described elsewhere. Pelletted extracellular virions were used in all experiments. Infectivity of R8102 was assayed as described in Montgomery, R. I., Warner, M. S., Lum, B. J. & Spear, P. G. (1996) Cell 87, 427–436 Antibodies. MAb R1.302 to PRR1 and MAb #3 to gD were described in Montgomery, R. I., Warner, M. S., Lum, B. J. & Spear, P. G. (1996) Cell 87, 427–436 and Lopez, M., Jordier, F., Bardin, F., Coulombel, L., Chabannon, C. & Dubreuil, P. (1997) in Leukocyte Typing VI, White cells differentiation antigens, ed. Kishimoto et al., (Garland Publishing), pp. 1081–1083. MAb HD1 to gD was from Goodwin Institute.

Construction, production and purification of soluble forms of HIgR and PVR receptors, sVCC(HIgR)-Fc, sV(HIgR)-Fc and sVCC(PVRα)-Fc (in accordance with FIG. 1). The entire extracellular region of HIgR (aa 1 to 334) was amplified by PCR with primers CFLPRR15 (CCGG AGAT ATCA TGGC TCGG ATGG GGCT TG) and CFLPRR13 (CCGA TCGG CCGA TGTG ATAT TGAC CTCC AC). The V domain (aa 1 to 144) was amplified with CFLPRR15 and CFLR1V (GTTG CGGC CGCC ATCA CCGT GAGA TTGA GCTG GC. The extracellular region of PVR (aa 1 to 330) was amplified with primers SBPVR5 (TTGA TCTG CAGA TGGC CCGA GCCA TGGC CGCC) and SBPVR3 (ATTT CTTT GCGG CCGC TTTG ACCT GGAC GGTC AGTT C). The PCR products were cloned in the Cos Fc Link (CFL) (Smith Kline Beecham Pharmaceuticals, PA, USA) vector (see Lopez, M., Aoubala, M., Jordier, F., Isardon, D., Gomez, S. & Dubreuil, P. (1998) Blood In press) and transfected in COS 1 with FuGENE 6 (Boehringer-Mannheim). The proteins were purified on Affigel protein A. Purification was monitored by the sandwich ELISA in 96 wells coated with antibody against human Fc (Sigma) and biotinylated R1.302 antibody. The CTLA4-Fc was provided by Dr. R. Sweet (SmithKline Beecham Pharmaceuticals, PA, USA).

Construction of V-TM(PRR1) and V(HIgR)-PVRα transmembrane receptor (in accordance with FIG. 1). The V domain of HIgR was amplified with PRR1V5 (TAAT AAGC TTAT GGCT CGGA TGGG GCTT GCGG GC) and PRR1V3(GGTG TAGG GGAA TTCC ATCA CCGT GAGA TTG). The transmembrane and intracytoplasmic region was amplified using primers PRR1IC5 (CAAT CTCA CGGT GATG GAAT TCCC CTAC ACC) and PRR1IC3 (ATTA GGAT CCCT ACAC GTAC CACT CCRT CTTFG G). Both PCR products were mixed in a second PCR reaction to get the final cDNA with primers PRR1V5 and PRR1IC3 (see Maroc, N., Rottapel, R., Rosnet, O., Marchetto, S., Lavezzi, C., Mannoni, P., Birnbaum, D. & Dubreuil, P. (1993) Oncogene 8, 909–918), cloned in the BamHI-HindIII sites of pcDNA3. For the chimeric receptor V(HIgR)-PVRa the V domain was amplified with primers PRR1V5 and R1VRV3 (GTGT TCTG GGGC TTGG CCAT CACC GTGA GATT G). The two C domains, transmembrane and intracytoplasmic regions of PVR, were amplified with primers R1VRCC5 (CAAT CTCA CGGT GATG GCCA AGCC CCAG AACA C) and R1VRCC3 (GTTA GGAT CCTC ACCT TGTG CCCT CTGT CTG). The 1253 bp cDNA fragment was cloned in BamHI/HindIII sites of the pcDNA3.

Sandwich ELISA for the soluble forms of HIgR/PRR1, sVCC(HIgR)-Fc and sV(HIgR)-Fc sVCC(HIgR)-Fc and sV(HIgR)-Fc were bound to microwells by means of anti-hIgG-Fc (Sigma), reacted with biotinylated MAb R1.302, followed by streptavidin-peroxidase and One Step ABTS (Pierce).

Competition by sVCC(HIgR)-Fc and sV(HIgR)-Fc on HIgR-mediated HSV-1 infectivity. Aliquots of R8102 were reacted with sVCC(HIgR)-Fc, sV(HIgR)-Fc or CTLA4-Fc for 1 h at 37° C., and absorbed for 2 h at 4° C. to cells. Virus was removed. Cells were overlaid with medium containing the sVCC(HIgR)-Fc and sV(HIgR)-Fc at the same concentrations used in the inoculum, and incubated for 16 h at 37° C. β-galactosidase was assayed as described in Geraghty, R. J., Krummenacher, C., Cohen, G. H., Eisenberg, R. J. & Spear, P. G. (1998) Science 280, 1618–1620.

In vitro binding of gD to soluble forms of HIgR/PRR1 by ELISA. gD was purified to homogeneity from HSV-1-infected BHK cells by affinity chromatography to Mab#30 (see Montgomery, R. I., Warner, M. S., Lum, B. J. & Spear, P. G. (1996) Cell 87, 427–436) immobilized to Affigel. Microwell plates were coated with 16 nM gD, reacted with sVCC(HIgR)-Fc or sV(HIgR)-Fc, followed by anti-human peroxydase (1:6000) and o-Phenylenediamine (Sigma). For competition ELISA, microwells were coated with gD. 10 nM sV(HIgR)-Fc (representing the saturating amount of sV(HIgR)-Fc for the gD-coated microwell—see FIG. 10A) were mixed with increasing concentrations of purified IgG of MAbs HD1, R1.302, or mouse IgG, and binding to gD as above. In FIG. 10B, dilution 1 corresponds to 1 μM purified IgG.

EXAMPLE 1

Monoclonal antibody R1.302 to HIgR/PRR1 reacts with an epitope mapped to the V domain of HIgR/PRR1.

Two soluble forms of HIgR/PRR1 and one of human poliovirus receptor-α (hPVRα) were constructed as detailed above and shown in FIG. 1. In sVCC(HIgR)-Fc, the three domains (one V and two C2) which constitute the ectodomain of HIgR and of PRR1 were fused to the Fc domain of human IgG1. In sV(HIgR)-Fc, the single V domain of HIgR/PRR1 was fused to IgG Fc. In sVCC (PVR)-Fc, the ectodomain of hPVRα was fused to the IgG1 Fc (data not shown). COS1 cells were transfected with the plasmid DNAs and the soluble receptors were purified from the culture medium by affinity chromatograhy to Protein A. The V domain, as defined here and below comprises the N-terminal 114 residues, after cleavage of the predicted signal sequence.

MAb R1.302 is capable of blocking HSV-1 infectivity in hamster cell lines which express either HIgR or PRR1 from transfected plasmids as well as in human cell lines like HEp-2, HeLa, human fibroblasts, U937, TF-1, etc, which express either one or the two isoforms. As HIgR and PRR1 share the ectodomain, the epitope recognized by MAb R1.302 must reside in the ectodomain of the molecules. FIG. 7 shows that the epitope recognized by MAb R1.302 resides in the V domain of the HIgR/PRR1. In a sandwich ELISA that measured the binding of MAb R1.302 to sVCC(HIgR)-Fc or sV(HIgR)-Fc, the antibody was capable of binding both molecules. The binding was highly specific as MAb R1.302 failed to bind soluble forms of hPVRα (FIG. 7) and of PRR2(HveB) (not shown), two structurally-related receptors belonging to the same immunoglobulin cluster (see Lopez, M., Eberlé, F., Mattei, M. G., Gabert, J., Birg, F., Bardin, F., Maroc, C. & Dubreuil, P. (1995) Gene 155, 261–265 and Eberlé, F., Dubreuil, P., Mattei, M. G., Devilard, E. & Lopez, M. (1995) Gene 159, 267–272 and also Lopez, M., Aoubala, M., Jordier, F., Isardon, D., Gomez, S. & Dubreuil, P. (1998) Blood In press), and to sCTLA4-Fc (data not shown), a chimeric protein carrying the V domain of the T cells costimulatory protein CTLA4 fused to IgG1 Fc. These results suggest that a major functional region of HIgR/PRR1 involved in HSV-1 entry into cells resides in the V domain.

EXAMPLE 2

A soluble form of HIgR/PRR1 consisting of the single V domain inhibits HSV-1 infectivity.

The following experiments show that the soluble truncated form containing the single V domain, sV(HIgR)-Fc, competed successfully with the full-length cell-bound HIgR resulting in inhibition of HSV-1 infectivity.

Replicate aliquots of the HSV-1 recombinant virus R8102, which carries a LacZ reporter gene fused to the immediate early α-27 promoter, were preincubated with increasing amounts of sV(HIgR)-Fc for 1 h at 37° C. and absorbed to the HIgR/cl 11 cells.

Infection was quantified after 16 h as α-gal activity. Positive control consisted of the soluble full-length receptor sVCC(HIgR)-Fc. Negative controls consisted of sVCC(PVR)-Fc and sCTLA4-Fc. As shown in FIG. 8A, the sV(HIgR)-Fc inhibited HSV-1 infectivity in a dose dependent manner, with an inhibition curve similar, although not exactly overlapping that obtained with sVCC(HIgR)-Fc. The inhibition was specific since sVCC(PVR)-Fc or sCTLA4-Fc had no significant inhibitory effect. The results in FIGS. 8B and C show that also in HEp-2 and HeLa cells, the sV(HIgR)-Fc competed with the resident cellular receptors and blocked R8102 infectivity.

The reason for the slight difference between the blocking effect of sVCC(HIgR)-Fc and of sV(HIgR)-Fc in HIgR- or PRR1-transformed cells and not in HeLa or HEp-2 cells is not clear at the moment.

The results are consistent with those of Example 1 showing that the V domain contains the epitope recognized by the MAb R1.302, capable of inhibiting virus infectivity, and allow to draw two conclusions. A major functional region in HSV-1 entry is located in the V domain of HIgR/PRR1. The interaction between HSV-1 and the functional region encoded in the V domain is crucial for virus infectivity.

EXAMPLE 3

The single V domain of PRR1 fused to its transmembrane domain or transferred to the CC-transmembrane-cytoplasmic domains of hPVRα is sufficient for HSV-1 infectivity.

First experiment (the receptor-deficient J1.1–2 cells resistant to HSV-1 infection were rendered susceptible when transfected with an engineered form of PRR1 in which the V domain and transmembrane and cytoplasmic regions were retained and fused together but the two C2 domains were deleted).

To ascertain if the V domain of HIgR/PRR1 was sufficient to mediate HSV-1 entry into cells, a construct was generated in which the two C2 domains of PRR1 were deleted and the single V domain was fused directly to its transmembrane-cytoplasmic domains, designated V-TM(PRR1). The J1.1–2 cells, shown above to be resistant to HSV infection because of lack of suitable receptors, were transfected with the plasmid DNA, subjected to neomycin G418 selection for two weeks, and assayed for susceptibility to R8102. V-TM (PRR1)/Q cells acquired susceptibility to R8102 infection, as detected by in situ X-gal staining (data not shown). The susceptibility correlated specifically with the V domain, as infectivity was abolished by MAb R1.302 capable of inhibiting infection and whose reactive epitope maps to the V domain (data not shown). The number of cells acquiring susceptibility was much lower in cultures expressing V-TM (PRR1) than in cultures expressing the full length HIgR or PRR1. This may be due either to a lower extent of expression of V-TM(PRR1) relative to the full length molecules or to a lower efficiency of the truncated molecule in conferring susceptibility to infection. To discriminate between these two possibilities the extent of expression was compared in V-TM(PRR1)- and HIgR-transfected cells by immunofluorescence with MAb R1.302. The number of fluorescent cells was found to be practically the same (data not shown), suggesting that the deleted version of PRR1 lacking the two C domains is less effective that the full length counterpart in-conferring susceptibility to HSV-1 infection. Parenthetically, the reactivity of MAb R1.302 to cells expressing the deleted and the full length versions of HIgR/PRR1 confirms that MAb R1.302 is directed to an epitope present in the V domain. Altogether the results demonstrate that the V domain of HIgR/PRR1 was sufficient to mediate HSV-1 entry into cells, although at reduced efficiency relative to full length receptor, and that susceptibility conferred by V-TM(PRR1) correlated specifically with the presence of the V domain.

Second experiment

To confirm this and to investigate the reasons for the lower efficiency of V-TM(PRR1), a second construct was generated in which the V domain of HIgR/PRR1 was transferred to CC-transmembrane-cytoplasmic regions of hPVR$_\alpha$. This receptor was chosen as acceptor of the HIgR/PRR1 V domain because it has an overlapping structure to that of HIgR (see Lopez, M., Eberlé, F., Mattei, M. G., Gabert, J., Birg, F., Bardin, F., Maroc, C. & Dubreuil, P. (1995) Gene 155, 261–265) but fails to mediate entry of any HSV-1 and -2 tested (see Geraghty, R. J., Krummenacher, C., Cohen, G. H., Eisenberg, R. J. & Spear, P. G. (1998) Science 280, 1618–1620). Therefore it represents the receptor functionally-inactive but structurally closer to HIgR/PRR1 available. FIG. 4C shows that V(HIgR)-PVRα transfected into the resistant J1.1–2 cells conferred susceptibility to HSV-1 infection, and had an efficiency comparable to that of full length HIgR (compare C and E). Infectivity was abolished by exposure of cells expressing V(HIgR)-PVRα to MAb R1.302 (FIG. 4D), demonstrating that the susceptibility acquired by V(HIgR)-PVRα was due to transfer of the V domain of HIgR/PRR1. The results confirm that the V domain of HIgR was sufficient to confer susceptibility, and in addition suggest that the CC backbone of this cluster of molecules augments the virus entry activity located in the V domain and/or participates in virus entry activity with other mechanisms.

EXAMPLE 4

The single V domain is sufficient for physical interaction with gD. The above data demonstrate that a major region of HIgR/PRR1 functional in HSV-1 entry resides in the V domain and that this domain is sufficient to mediate HSV-1 infectivity. gD binds to a soluble form of HveC(PRR1) containing the entire ectodomain (see Krummenacher, C., Nicola, A. V., Whitbeck, J. C., Lou, H., Hou, W., Lambris, J. D., Geraghty, R. J., Spear, P. G., Cohen, G. H. & Eisenberg, R. J. (1998) J Virol 72, 7064–7074). Here we investigated whether the single V domain of HIgR/PRR1 was sufficient for the physical interaction with gD. For this assay, gD was immobilized to microwells and then reacted with the soluble receptor consisting of the single V-domain, sV(HIgR)-Fc, or with the full-length sVCC(HIgR)-Fc as a positive control. The results in FIG. 10A demonstrate that sV(HIgR)-Fc bound gD in a dose dependent manner, with a curve essentially similar to that obtained with sVCC(HIgR)-Fc. There was an about 30% reduction in the level of saturable binding with sV(HIgR)-Fc relative to sVCC (HIgR)-Fc, suggesting a somewhat higher efficiency in the binding to gD for the full length molecule. The control unrelated molecules CTLA4-Fc or BSA did not bind gD. Specificity of the binding was next measured in a competitive ELISA. A fixed amount of sV(HIgR)-Fc, giving a saturable binding to immobilized gD (see FIG. 10A) was preincubated with increasing concentrations of IgG from MAb R1.302 to HIgR/PRR1, or from MAb HD1, a monoclonal antibody to HSV gD with potent neutralizing activity on HSV infectivity (see Pereira, L., Klassen, T. & Baringer, J. R. (1980) Infect Immun 29, 724–732) and with ability to compete with the binding of PRR1(HveC) to virions in vitro (see Krummenacher, C., Nicola, A. V., Whitbeck, J. C., Lou, H., Hou, W., Lambris, J. D., Geraghty, R. J., Spear, P. G., Cohen, G. H. & Eisenberg, R. J. (1998) J Virol 72, 7064–7074.), or with purified mouse IgGs, as control. As can be seen from FIG. 10B, both the monoclonal antibody to HIgR, and the neutralizing monoclonal antibody HD1 to gD competed with the binding of gD to the soluble V domain of HIgR/PRR1, demonstrating that the in vitro binding of the V domain to gD was highly specific. The results of these two assays indicate that the V domain of HIgR/PRR1 was sufficient for specific binding to gD. The results confirm and extend the finding that the gD region recognized by HIgR/PRR1 contains the antigenic site Ia (see Krummenacher, C., Nicola, A. V., Whitbeck, J. C., Lou, H., Hou, W., Lambris, J. D., Geraghty, R. J., Spear, P. G., Cohen, G. H. & Eisenberg, R. J. (1998) J Virol 72, 7064–7074.). Thus, it is demonstrated that a soluble form of HIgR/PRR1 consisting of the single V domain interacted physically with gD in an in vitro binding assay. The binding was specific as it was competed by monoclonal antibodies to each partner with ability to neutralize HSV infectivity. Thus, monoclonal antibody R1.302 to HIgR/PRR1 competed with the ability of gD to bind to the receptor. In a similar fashion, the monoclonal antibody HD1 to gD with potent neutralizing activity on virion infectivity competed with the binding of gD to its receptor. It can be noted that MAb HD1 recognizes antigenic site Ia of gD, according to the classification of Cohen and Eisenberg (Muggeridge, M. I., Isola, V. J., Byrn, R. A., Tucker, T. J., Minson, A. C., Glorioso, J. C., Cohen, G. H. & Eisenberg, R. J. (1988) J Virol 62, 3274–3280). The results further indicate that the gD region which interacts with the V domain of HIgR/PRR1 contains the antigenic site Ia, in agreement with the finding that monoclonal antibodies to this site block binding of PRR1(HveC) to virions, and that the gD region interacting with HIgR/PRR1 does not exactly overlap with that recognized by HveA, which recognizes antigenic sites Ib and VII, but not Ia (see Nicola, A. V., Ponce de Leon, M., Xu, R., Hou, W., Whitbeck, J. C., Krummenacher, C., Montgomery, R. I., Spear, P. G., Eisenberg, R. J. & Cohen, G. H. (1998) J Virol 72, 3595–3601).

EXAMPLE 5

Materials and Methods

Cells and viruses. J1.1–2 cells, as described above, a derivative of BHKtk-cells devoid of the receptors for HSV entry, and J cells expressing HIgR, HveC/PRR1, or nectin2/PRR2α-, derived by transfection of HIgR, HveC/PRR1, or nectin2/PRR2α cDNA were described. Cells were grown in Dulbecco's modified Eagle medium (DME) supplemented with 5% fetal calf serum, and, where appropriate, with neomycin G418. A derivative of nectin2/PRR2α cells harboring a Lac-Z gene under the 27 promoter was also described (lopez2000), HSV-1(F), its recombinant R8102 carrying a Lac-Z gene under the control of the α27 promoter inserted between $U_L3$ and $U_L4$ genes, were described above. Viruses were grown and titrated in Vero cells. Extracellular virions were obtained by ultracentrifugation of infected cell medium. Transfection of HSV-1 DNA, purified by NaI gradient, was performed with Lipofectamine (GIBCO) according to the manufacturer instructions. Plaques were detected 2–3 days after infection by fixation, followed by immunostaining with polyclonal antibody to gM, horseradish peroxidase-conjugated anti-rabbit IgG antibody and DAB (3,3'-diamonobenzidine tetrahycholoride). In cells infected with R8102, or carrying α27-Lac-Z, plaques were detected by β-galactodisidase (β-gal) activity after X-Gal (5-bromo-4-chloro-3-indolyl-β-D-galctopiranoside) staining (ref mongomery cocchi a). Pictures were taken in an Axiophot Zeiss microscope. Quantification of plaque formation was performed by two methods. Wells containing immunostained plaques were scanned in a scanner, and the image imported by Photoshop software. The percentage of stained cells in the monolayer was calculated by means of the Istogram program in Photoshop. The inhibitory effect of antibodies was expressed as percentage relative to untreated cultures. Alternatively, for plaques detected by Lac-Z, cells were grown in 96 well trays, in triplicates. At 48 h after infection, cells were solubilized and reacted with ONPG (O-nitrophenyl-β-D-galactopiranoside) for quantitative detection of β-galactosidase activity, followed by reading the O.D. at 405 nm in a BIO-Rad Elisa reader.

HIgR and HveC mediate cell-to-cell spread of HSV-1(F).

In order to asses whether HveC and/or HIgR mediate cell to cell spread of HSV-1(F), first it was tested whether cell-to-cell spread occurs in J1.1–2 cells, which do not express HIgR, HveC, PRR2α and δ, HveA homologs, or in their derivatives expressing constitutively HveC or HIgR. J1.1.–2 cells were transfected with the DNA of HSV-1(F) (to overcome the lack of receptors for virus entry), or its derivative R8102, carrying α27-Lac Z. HIgR and HveC cells were either transfected or infected. Plaque formation was detected 2–3 days later by immunostaining or β-gal staining. The results in show that in J cells plaques were not formed, and infected cells consisted of single cells, or very small aggregates. By contrast, when HIgR or HveC expressing cells were infected with HSV-1(F) (or transfected with the viral DNA), plaques were readily observed, with no detectable difference among the latter two cell lines.

Plaque formation in HIgR or HveC cells was dependent upon expression of the receptors, as incubation of infected cells with MAb R1.302 to HIgR/HveC, from 4 h after infection till fixation, reduced the plaque size to small aggregates or single cells. An irrelevant monoclonal antibody had small effect on the plaque size, rather plaques appeared less compact. As expected, the number of plaques in HIgR or in HveC cells exposed to Mab R1.302, scored by counting the single cells and the small aggregates, did not differ from the number of plaques scored in the cultures untreated, or exposed to the irrelevant monoclonal antibody (data not shown). In order to quantify the effect of MAb R1.302, HIgR-cells infected with R8102 were exposed to increasing amounts of purified IgGs from Mab R1.302, or to control pooled mouse immunoglobulins. Plaque formation after 48 h was detected as β-gal expression. FIG. 11A shows that MAb R1.302 inhibited plaque formation in a dose-dependent fashion; 50% inhibition. At the same concentrations, control mouse immunoglobulins reduced to a much lower extent. The concentrations required to inhibit plaque formation were higher than those required to block HSV infectivity in the same cells.

The V domain of HIgR/HveC is functional in cell-to-cell spread.

It has ascertain that the v domain of HIgR is the region functional in HSV entry, and is sufficient for this activity and that the V domain is involved also in cell-to-cell spread. To this end, it was determined whether a soluble form of HveC/HIgR carrying the entire ectodomain (VCC1-Fc), or the single V domain (V1-Fc), could compete with cell-bound receptor and block cell-to-cell spread of virus. Infected HIgR cells were incubated with VCC1-Fc or V1-Fc, starting at 4 h after infection. This reduced plaque formation in a dose dependent manner (FIG. 11B).

Cell-to-cell spread mediated by HIgR/HveC in human cell lines. The contribution of HveC/HIgR to cell-to-cell spread of HSV-1(F) in the human cell lines, HEp-2, 143tk-, and human fibroblasts was determined by assaying the effect of antibody R1.302 on plaque formation. The results indicate that in 143tk- and HEp-2 cells, the plaques decreased in size, although in HEp-2 cells to a lower extent than in the HIgR or HveC-expressing cells, or in 143tk-cells. The results indicate that HveC and/or HIgR mediates HSV cell-to-cell spread in human cell lines, and underscores that in humans, upon reactivation from latency in sensory neurons, HIgR and or HveC serve as receptors for the transmission of virus from nerve endings to mucoutaneous tissues.

What is claimed is:
1. A purified and isolated DNA sequence comprising a 35 nucleotide sequence designated as SEQ ID No 2.

* * * * *